(12) United States Patent
Hart et al.

(10) Patent No.: US 9,720,259 B2
(45) Date of Patent: Aug. 1, 2017

(54) EYEWEAR PUPILOMETER

(71) Applicants: William Hart, Aptos, CA (US);
Edmond Arthur DeFrank, Northridge, CA (US); Nicolas DeFrank, Northridge, CA (US); Antonio DeFrank, Northridge, CA (US); Allen Mark Jones, Imperial Beach, CA (US)

(72) Inventors: William Hart, Aptos, CA (US);
Edmond Arthur DeFrank, Northridge, CA (US); Nicolas DeFrank, Northridge, CA (US); Antonio DeFrank, Northridge, CA (US); Allen Mark Jones, Imperial Beach, CA (US)

( * ) Notice: Subject to any disclaimer, the term of this patent is extended or adjusted under 35 U.S.C. 154(b) by 0 days.

(21) Appl. No.: 14/881,921

(22) Filed: Oct. 13, 2015

(65) Prior Publication Data
US 2016/0103338 A1 Apr. 14, 2016

Related U.S. Application Data

(60) Provisional application No. 62/063,194, filed on Oct. 13, 2014.

(51) Int. Cl.
*A61B 3/14* (2006.01)
*G02C 11/00* (2006.01)
(Continued)

(52) U.S. Cl.
CPC .............. *G02C 11/10* (2013.01); *A61B 3/112* (2013.01); *A61B 3/14* (2013.01); *G02C 7/04* (2013.01); *A61B 3/12* (2013.01); *A61B 5/18* (2013.01)

(58) Field of Classification Search
CPC ........... G02C 11/10; G02C 7/04; A61B 3/112; A61B 3/14; A61B 5/18; A61B 3/12; A61B 3/145; A61B 3/1225; A61B 3/102
(Continued)

(56) References Cited

U.S. PATENT DOCUMENTS

2008/0044063 A1* 2/2008 Friedman ............. A61B 3/1216
382/117
2010/0103368 A1* 4/2010 Amirparviz ...... B29D 11/00826
351/158

(Continued)

*Primary Examiner* — Stephone B Allen
*Assistant Examiner* — Rahman Abdur
(74) *Attorney, Agent, or Firm* — Edmond DeFrank

(57) ABSTRACT

The embodiments disclose an apparatus including an eyewear pupilometer for detecting, measuring and processing a wearer's pupil movement and size, for detecting and processing retinal images, for detecting and processing a wearer's field of view, for broadcasting alerts, for pre-diagnostic screening, for overriding vehicle operation and for measuring, recording and transmitting circadian responses, at least one eyewear pupilometer module including a lens fiber optic camera module, an image processor module, a retinal image infrared detector module, an outward camera module, at least one alert module, an alert light and message projector, a WI-FI module, an automated pullover module, an automated steering module, fiber optic & data cables, a contact lens pupilometer image, sensor and processor module, and at least one eyewear pupilometer module coupled to and/or embedded into eyewear frames and lenses, contact lenses, a vehicle wind shield and protective covers for hand held devices and laptop computers.

17 Claims, 37 Drawing Sheets

(51) Int. Cl.
*A61B 3/11* (2006.01)
*G02C 7/04* (2006.01)
*A61B 3/12* (2006.01)
*A61B 5/18* (2006.01)

(58) Field of Classification Search
USPC .......................................................... 351/206
See application file for complete search history.

(56) References Cited

U.S. PATENT DOCUMENTS

| | | | | |
|---|---|---|---|---|
| 2012/0038881 | A1* | 2/2012 | Amirparviz | G02C 7/04 351/159.02 |
| 2012/0274899 | A1* | 11/2012 | Wang | A61B 3/12 351/206 |
| 2013/0346168 | A1* | 12/2013 | Zhou | G06F 1/163 705/14.4 |

* cited by examiner

EYEWEAR PUPILOMETER CONTACT LENS SHOWN ON AN EYE WITH A CONSTRICTED PUPIL — 3000

EYEWEAR PUPILOMETER CONTACT LENS SHOWN ON AN EYE WITH A DILATED PUPIL — 3010

EYEWEAR PUPILOMETER

CROSS-REFERENCE TO RELATED APPLICATIONS

This application is based on U.S. Provisional Patent Application Ser. No. 62/063,194 filed Oct. 13, 2014, entitled "EYEWEAR PUPILOMETER", by William Hart, et. al.

BACKGROUND

Patient eye examinations may include a brief check of the pupil response and a retinal image. The typical eye examinations may be months apart and the actual examine a "snapshot" of the patient's eyes at a given moment and under fixed conditions at that moment. Pupil response may indicate a person's level of drowsiness and the person's ability to function normally for example safely drive a vehicle.

One in 10 motorists admits falling asleep behind the wheel. One in 10 drivers has fallen asleep while driving in the past 12 months, equating to 3.4 million motorists driving a total distance of more than 55,000 miles. So says LV=car insurance whose research has also revealed that these motorists drive at an average speed of 50 mph when they nod-off, in which time they cover an average distance of 26 meters—the equivalent of two double-decker buses. Official police figures, obtained via a Freedom of Information request, reveal that there were more than 3,357 fatigue-related road accidents recorded over the past five years. Yet only 15 police forces out of 51 were able to provide this information and so the actual figure is likely to be closer to 11,000, according to the firm. Of the 3.4 million motorists who confessed they had fallen asleep behind the wheel in the past 12 months, one in 20 (5%) say they had an accident and almost a third (29%) either swerved or veered off the road while dozing.

Many motorists admit they sometimes risk driving despite knowing they are too tired to safely operate a vehicle. Close to a third (28%) say they have got behind the wheel of their car while they were feeling drowsy and a fifth (19%) admit they've hardly been able to keep their eyes open while driving. The monotony of motorways and dual carriageways combined with a lack of sleep, are the main reasons cited for dozing while driving. Others blame long distance driving to get to a holiday destination, feeling tired after a late shift at work or feeling drowsy after taking medication. Typically drivers fall asleep behind the wheel at night when there is not much light and fewer cars on the road. Over half (56%) of those who fell asleep while driving say it happened between 8 pm and 6 am. The issue is particularly prevalent in male drivers, who are nearly three times as likely to fall asleep at the wheel than their female equivalents (33% of men compared to 12% of women).

A managing director of LV=car insurance, commented: The research shows that when people fall asleep behind the wheel it is usually because they are on a long monotonous road and haven't taken a break, or they haven't had enough sleep the night before. Falling asleep while driving, even momentarily, is extremely dangerous but taking regular breaks from driving can help prevent it. If you know you are going to be driving long distance, plan ahead and make sure you have sufficient time to rest.

It should be noted that various clinical conditions, especially neurological and ocular diseases, as well as numerous medications, may interfere with the measurements. Furthermore, a number of physiological parameters, such as the intensity of retinal illumination, the level of patient's alertness, the intensity of ambient light, as well as the time of day that the examination is performed may alter the obtained values.

SUMMARY

Neuroptic studies have been performed for multiple sleep latency test (MSLT) using pupilometry to assess alertness in hypersomnolent patients and normal volunteers. The studies examined both groups by pupilometry and their sleepiness was assessed by using the multiple sleep latency test (MSLT). The results showed a strong correlation in the findings of the pupilometry and MSLT and concluded the usefulness of pupilometry for the diagnosis of pathologic sleepiness in individual patients.

Patients were classified as having 'mild', 'moderate', or 'severe' sleepiness, based on their mean MSLT sleep latency. Several dynamic variables of pupil diameter were calculated from the pupilograms and correlated with the mean MSLT sleep latency, and were compared between severity groups of patients and the well-rested normal subjects. Results: All but two pupilometric variables were significantly correlated with sleep latency. All except the same two pupilometric variables of the sleepiest group were significantly different from those of normal subjects. Conclusions: Pupilometry is clearly associated with differences in alertness between groups of patients.

According to a Georgetown University study where clinical outcomes showed a manual exam may assess pupil size accurately; distinguishing from a brisk or nonreactive pupil is problematic. The manual exam has a median error in pupillary size measurement (0.55 mm) that is 2× that of the Pupilometer (0.23 mm) and is more susceptible to errors and differences. Pupillary signs could be detected earlier with a portable infrared Pupilometer. "Performing frequent pupil assessments provide critical and time-sensitive information regarding new or worsening intracranial pathology; therefore, an accurate examination is essential. Automated Pupilometry may be useful in providing ICU nurses with a precise and reliable measurement or pupil size and reactivity."

Using a Pupilometer in Critical Care provides pupil assessment which is a fundamental part of the neurological examination. Size and reactivity to light of each pupil should be recorded. The eyewear pupilometer allows continual pupil assessments allowing health care providers to obtain immediate notification and data to treatment changes immediately not later when an infrequent assessment is scheduled.

Changes in pupil assessments parameters may represent the only detectable sign of neurological deterioration in some patients. Pupilometry has been widely employed in the evaluation of a large number of pathological conditions, including intracranial pathology. The pupillary examination may provide critical information related to new or worsening intracranial pathology and facilitate prompt intervention to minimize further neuronal damage. Studies have found that an automated pupilometer is more accurate and reliable than the manual examination in measuring pupil size and reactivity. The eyewear pupilometer is an automated means of measuring pupil size and reactivity without a doctor's office visit, without blocking a user's vision, forced medication dilation of the pupils, requiring a light stimulus to be projected onto the retina or surface of the eye, and providing pupilometer examinations continual and/or frequent pupillary assessments.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the embodiments.

General Overview:

It should be noted that the descriptions that follow, for example, in terms of eyewear pupilometer is described for illustrative purposes and the underlying system can apply to any number and multiple types of vision eyewear. In one embodiment, the eyewear pupilometer can be configured using optical fibers to communicate images. The eyewear pupilometer can be configured to include pupil movement and size in visible light and can be configured to include pupil movement and size in infrared wavelengths using the present invention.

Figure 1:
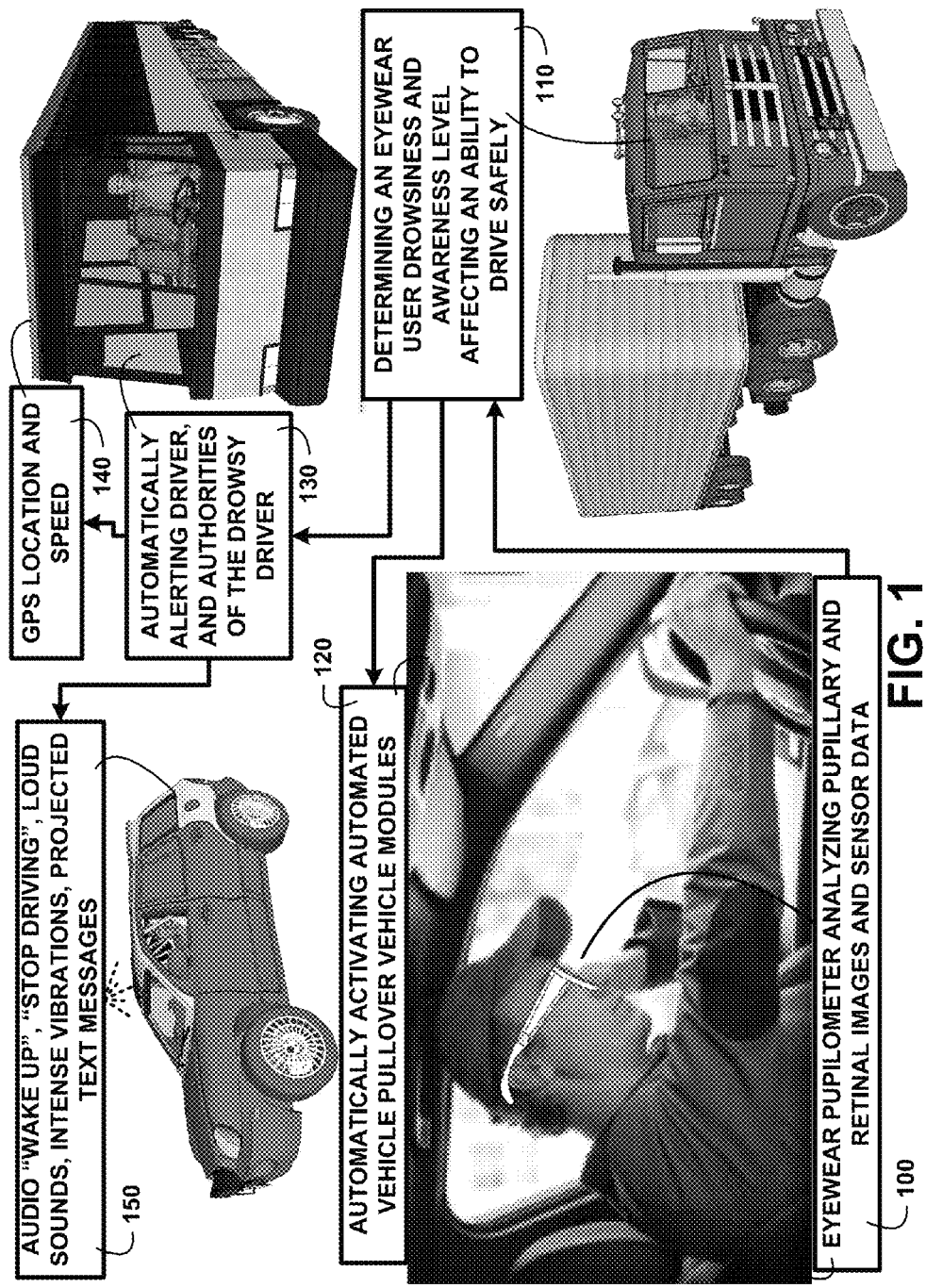
FIG. 1 shows a block diagram of an overview of an eyewear pupilometer of one embodiment.

FIG. 1 shows a block diagram of an overview of an eyewear pupilometer of one embodiment. FIG. 1 shows a driver wearing a pair of eyewear pupilometer glasses. The driver may be behind the wheel of an automobile including an SUV, a bus including a tour bus, a semi-truck and trailer or type of motor vehicle. The eyewear pupilometer analyzing pupillary and retinal images and sensor data 100 will provide the driver and others with a valid assessment of the driver's condition to drive safely of one embodiment.

The eyewear pupilometer analysis is used for determining an eyewear user's drowsiness and awareness level affecting an ability to drive safely 110. When the eyewear pupilometer analysis determines a driver is drowsy, not alert or sleeping the eyewear pupilometer activates alert modules that are used for automatically alerting driver and authorities of the drowsy driver 130. The alert to authorities includes GPS location and speed 140 of the vehicle. Alerts to the driver includes audio "wake up", "stop driving", loud sounds, intense vibrations, projected text messages 150 of one embodiment.

Should the driver not respond to the alerts and become alert the eyewear pupilometer initiates automatically activating automated vehicle pullover vehicle modules 120. The automated vehicle pullover vehicle modules override the driver's control of the vehicle and monitor surrounding traffic to safely pull the vehicle over to the shoulder of the road and stop the vehicle. The vehicle will not restart until the driver's pupillary assessments being performed by the eyewear pupilometer reaches an alert status. Should the driver remove the eyewear pupilometer the alertness signal will not be sent and the vehicle will remain in a locked-out restart condition of one embodiment.

A comprehensive ongoing analysis of a person's eye conditions can be used to determine a person's physical state and mental interest in what is being seen. A comprehensive analysis may include eye pupils, including pupil size, eye movements, blood circulation, oxygenation in the optic blood vessels and other data. The analysis detecting and measuring the eye conditions may be used for determining fatigue and tiredness, level of awakeness, drowsiness and attentiveness. The analysis can also be used to help diagnose health conditions, a person's interest level in something or someone being seen by the person of one embodiment.

For example should the eye condition analysis detect the person's pupil size is larger than normal in intense light it may indicate the person is drowsy due to sleepiness. Typically when a person is sleepy the pupil does not react as fast or normally due to parasympathetic responses brought on by being tired. A person should not drive a moving vehicle including a car, truck, boat or aircraft when they are so tired their eye pupil response for example pupil size is not responding normally. They may fall asleep or dose off while operating the vehicle. The present invention is a pupilometer used to measure eye conditions and integrated into eyewear of one embodiment.

Figure 2:
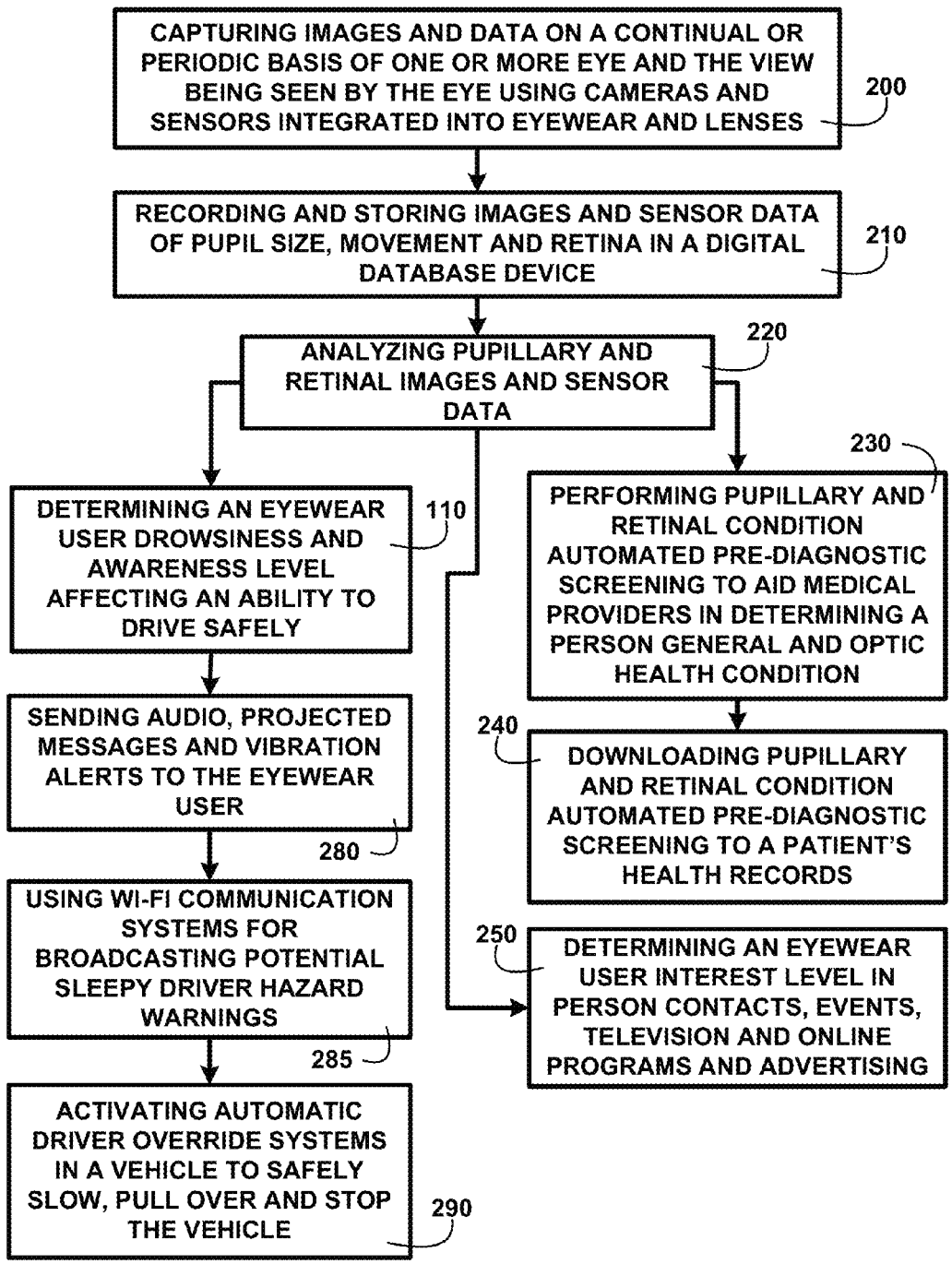
FIG. 2 shows a block diagram of an overview flow chart of an eyewear pupilometer of one embodiment.

FIG. 2 shows a block diagram of an overview flow chart of an eyewear pupilometer of one embodiment. FIG. 2 shows capturing images and data on a continual or periodic basis of one or more eye and the view being seen by the eye using cameras and sensors integrated into eyewear and lenses 200. In one embodiment the cameras and sensors are integrated into eye glasses and form the eyewear pupilometer. The eyewear pupilometer include modules used for recording and storing images and sensor data of pupil size, movement and retina in a digital database device 210 of one embodiment.

The eyewear pupilometer modules include modules used for analyzing pupillary and retinal images and sensor data 220 including digital processors. In one embodiment the eyewear pupilometer is used for determining an eyewear user drowsiness and awareness level affecting an ability to drive safely. When an eyewear user drowsiness and awareness level analysis determines it is unsafe for driving the vehicle the eyewear pupilometer is used for sending audio, projected messages and vibration alerts to the eyewear user 280 driver. A driver's drowsiness may trigger using WI-FI communication systems for broadcasting potential sleepy driver hazard warnings 285 using the eyewear pupilometer modules. Should the driver not positively respond to the alerts the eyewear pupilometer modules are used for activating automatic driver override systems in a vehicle to safely slow, pull over and stop the vehicle 290 of one embodiment.

The eyewear pupilometer modules may be used for performing pupillary and retinal condition automated pre-diagnostic screening to aid medical providers in determining a person general and optic health condition 230. The automated pre-diagnostic screening data is configured for downloading pupillary and retinal condition automated pre-diagnostic screening to a patient's health records 240 and medical provider of one embodiment.

In one embodiment the eyewear pupilometer modules captured and recorded pupillary responses may be used for determining an eyewear user interest level in person contacts, events, television and online programs and advertising 250. The user GPS location can be used for ad selection and display for local businesses and services. For example a user driving down a road can be displayed an ad for a local pizza restaurant coming up on the user's right side of the road way just ahead. If the user turns their head to the right, looks to the right the movement and eye movement are recorded for the ad, showing the user may be hungry or likes pizza. If the user circadian responses to pizza restaurant ad and visually searches for the restaurant being advertised include for example enlarged pupillary response then this is and indicator the user has interest. The ad can be followed up with a discount offer to further entice the user to stop at the restaurant and dine. If on the other hand the user shows no circadian responses and makes no effort to make visual sighting of the restaurant then this may indicate the user may not be hungry or does not like pizza. Subsequent ads can then filter out pizza and display other types for restaurants in the local area along the GPS determined user route.

This may assist the user, advertisers and other interested parties in determining products, environments, colors and individuals that registered high interest for the eyewear user. The outward view of the user through the eyewear pupilometer may capture images in bright and darkened ambient light. The image capture may be processed in a face recognition processing module to aid the user in identifying someone whose name they forgot, or criminals that may accost the user of one embodiment.

Figure 3:
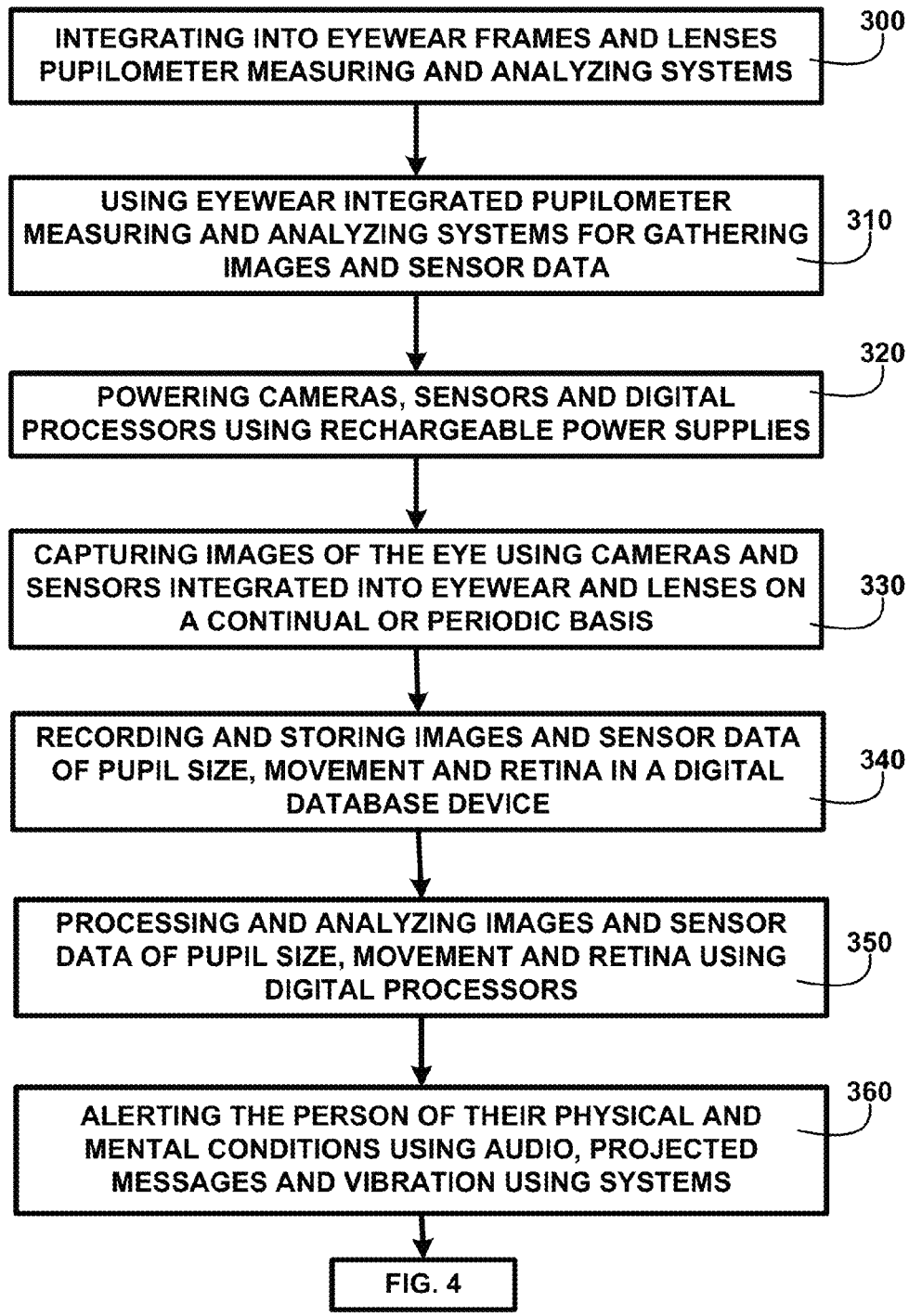
FIG. 3 shows a block diagram of an overview flow chart of eyewear pupilometer modules and systems of one embodiment.

Eyewear Pupilometer Modules:

FIG. 3 shows a block diagram of an overview flow chart of eyewear pupilometer modules and systems of one embodiment. FIG. 3 shows integrating into eyewear frames and lenses pupilometer measuring and analyzing systems 300 modules. Using eyewear integrated pupilometer measuring and analyzing systems for gathering images and sensor data 310. Powering cameras, sensors and digital processors using rechargeable power supplies 320. Capturing images of the eye using cameras and sensors integrated into eyewear and lenses on a continual or periodic basis 330. Recording and storing images and sensor data of pupil size, movement and retina in a digital database device 340. Processing and analyzing images and sensor data of pupil size, movement and retina using digital processors 350.

Alerting the person of their physical and mental conditions using audio, projected messages and vibration using systems 360. The descriptions continue in FIG. 4 of one embodiment.

Figure 4:
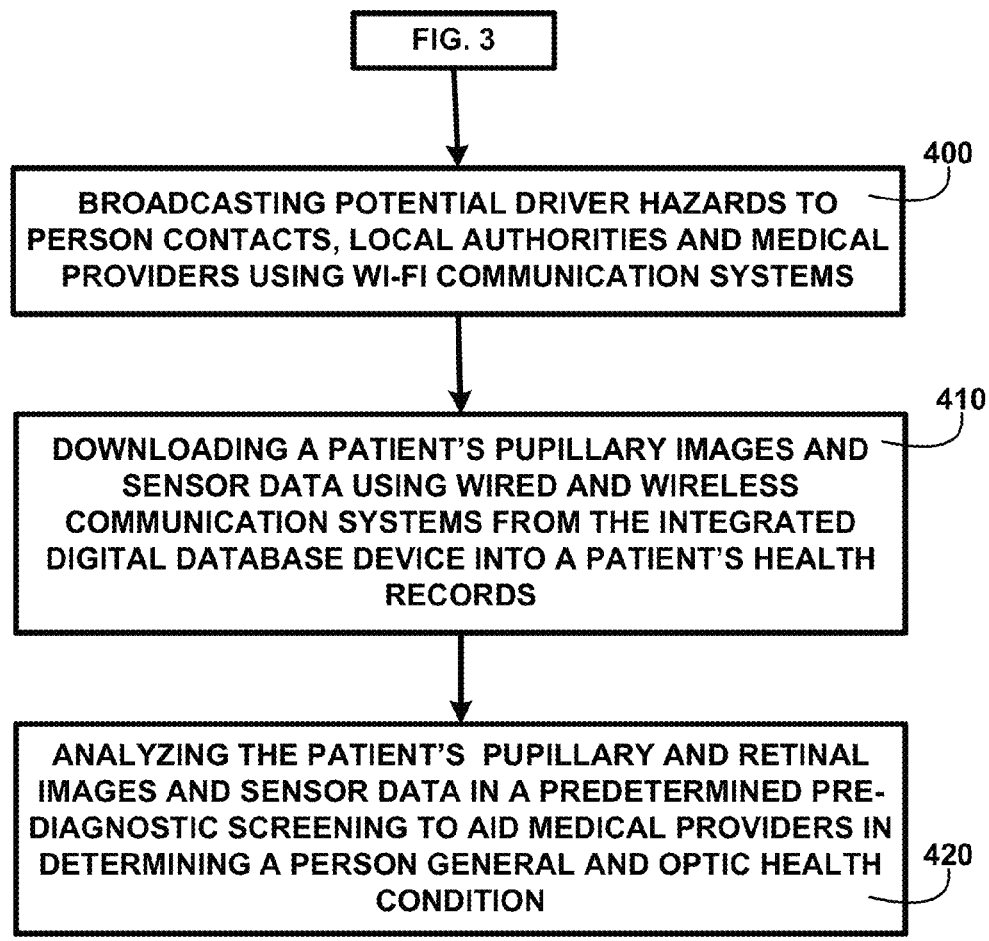
FIG. 4 shows a block diagram of an overview flow chart of eyewear pupilometer modules for broadcasting alerts and pre-diagnostic screening of one embodiment.

Broadcast and Pre-Diagnostic Screening Modules:

FIG. 4 shows a block diagram of an overview flow chart of eyewear pupilometer modules for broadcasting alerts and pre-diagnostic screening of one embodiment. FIG. 4 shows continuing from FIG. 3 eyewear pupilometer modules used for broadcasting potential driver hazards to person contacts, local authorities and medical providers using WI-FI communication systems 400 modules. Also shown in one embodiment are eyewear pupilometer modules used for downloading a patient's pupillary images and sensor data using wired and wireless communication systems from the integrated digital database device into a patient's health records 410 and the patient's medical provider. The eyewear pupilometer modules are configured for analyzing the patient's pupillary and retinal images and sensor data in a predetermined pre-diagnostic screening to aid medical providers in determining a person general and optic health condition 420 of one embodiment.

Figure 5:
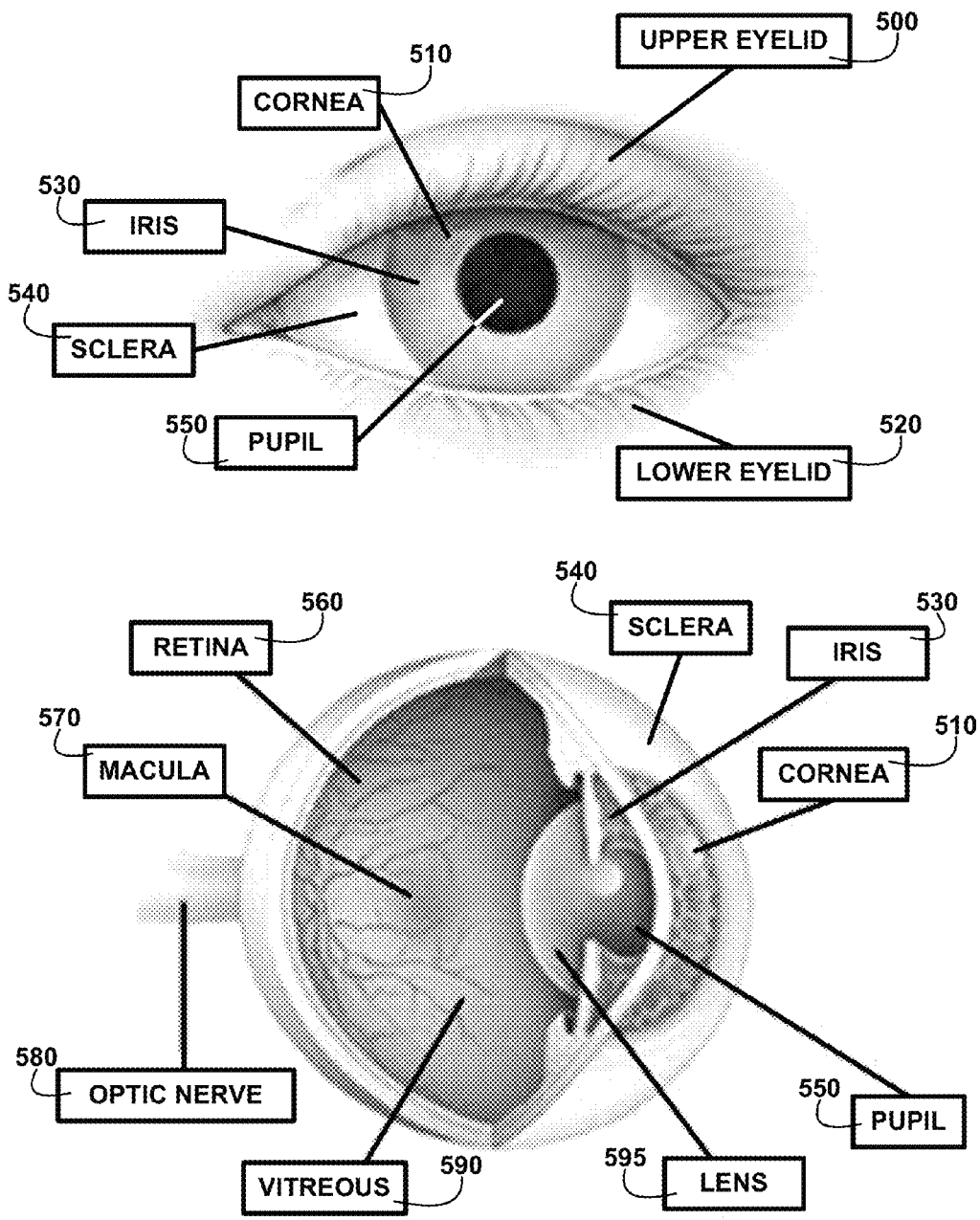
FIG. 5 shows for illustrative purposes only an example of parts and regions of a human eye of one embodiment.

Exterior Eye Parts:

FIG. 5 shows for illustrative purposes only an example of parts and regions of a human eye of one embodiment. FIG. 5 shows the exterior parts of a human eye include the pupil 550, iris 530, sclera 540, cornea 510, upper eyelid 500 and lower eyelid 520. The interior of the eye includes the optic nerve 580, retina 560, macula 570, vitreous 590 and lens 595 of one embodiment.

Figure 6A:
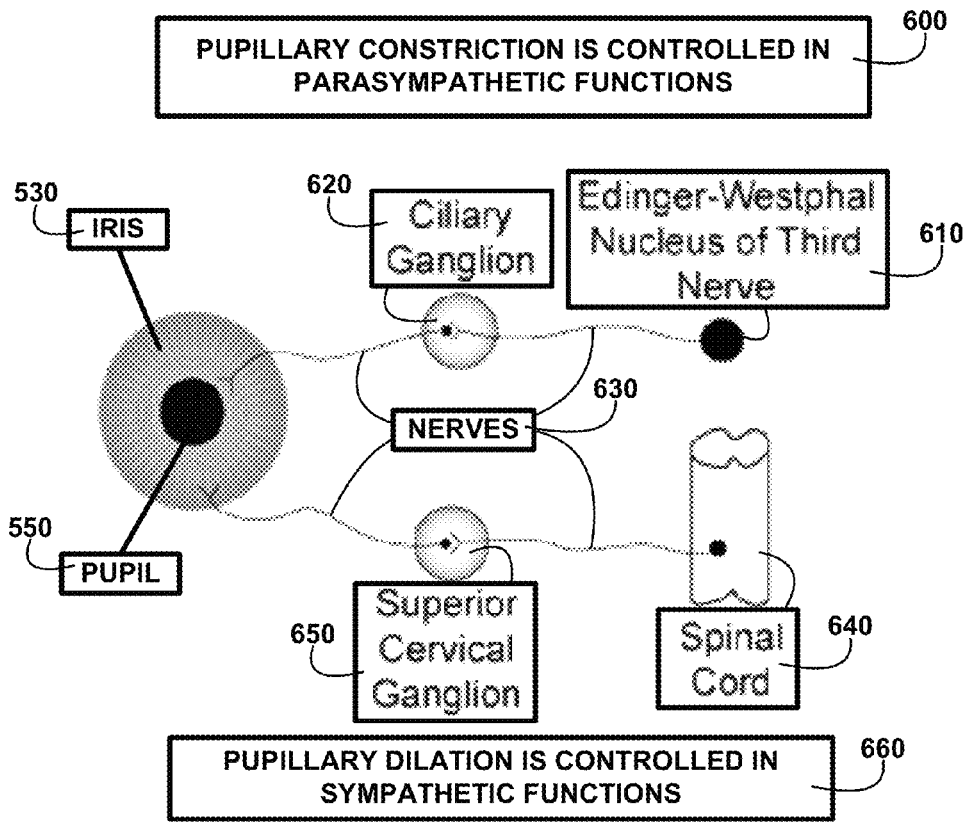
FIG. 6A shows for illustrative purposes only an example of physiological pupillary control features of one embodiment.

Pupillary Control Features:

FIG. 6A shows for illustrative purposes only an example of physiological pupillary control features of one embodiment. FIG. 6A shows pupillary constriction is controlled in parasympathetic functions 600. The pupil is constricted through nerves in the iris 530 that are activated by ciliary ganglion 620 signaled by Edinger-Westphall nucleus of third nerve 610. The pupillary dilation is controlled in sympathetic functions 660. The iris 530 is activated to open the pupil 550 through nerves 630 connected to the iris 530. Superior cervical ganglions 650 are triggered by nerve signals from the spinal cord 640 of one embodiment.

The physiology behind a "normal" pupillary constriction is a balance between the sympathetic and parasympathetic nervous systems. Parasympathetic innervation leads to pupillary constriction. A circular muscle called the sphincter pupilae accomplishes this task. The fibers of the sphincter pupilae encompass the pupil. The pathway of pupillary constriction begins at the Edinger-Westphal nucleus near the occulomotor nerve nucleus. The fibers enter the orbit with CNIII nerve fibers and ultimately synapse at the ciliary ganglion of one embodiment.

Sympathetic innervation leads to pupillary dilation. Dilation is controlled by the dilator pupilae, a group of muscles in the peripheral ⅔ of the iris. Sympathetic innervation begins at the cortex with the first synapse at the ciliospinal center (also known as Budge's center after German physiologist Julius Ludwig Budge). Post synaptic neurons travel down all the way through the brain stem and finally exit through the cervical sympathetic chain and the superior cervical ganglion 650. They synapse at the superior cervical ganglion 650 where third-order neurons travel through the carotid plexus and enter into the orbit through the first division of the trigeminal nerve of one embodiment.

Figure 6B:
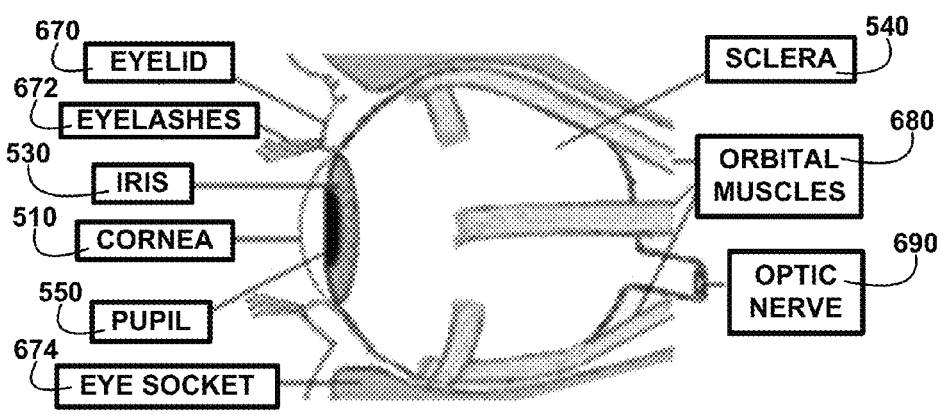
FIG. 6B shows for illustrative purposes only an example of eye musculature of one embodiment.

Eye Musculature:

FIG. 6B shows for illustrative purposes only an example of eye musculature of one embodiment. FIG. 6B shows the exterior parts and regions of the eye including the eyelid 670, eyelashes 672, iris 530, cornea 510 and pupil 550 which are in part controlled by the eye musculature. Located in the eye socket 674 are the interior regions of the sclera 540, the optic nerve 690 and orbital muscles 680. The orbital muscles 680 control movements of the eye orbit for example movements up and down and side to side of one embodiment.

Figure 7:
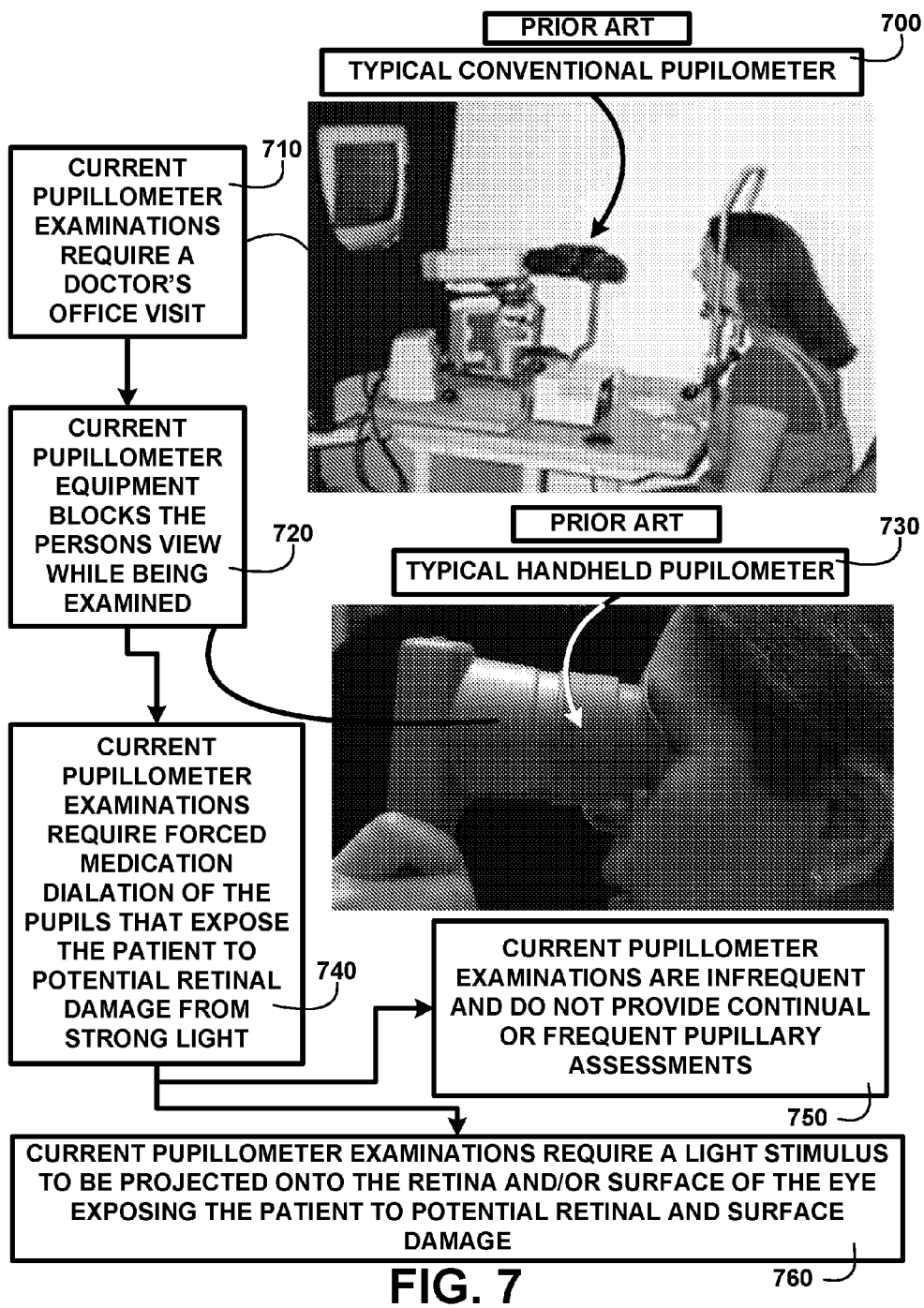
FIG. 7 shows for illustrative purposes only an example of current pupilometer examination equipment of one embodiment.

Current Pupilometer Examination Equipment:

FIG. 7 shows for illustrative purposes only an example of current pupilometer examination equipment of one embodiment. FIG. 7 shows a typical conventional pupilometer 700 and a typical handheld pupilometer 730. Current pupilometer examinations require a doctor's office visit 710. Current pupilometer equipment blocks the persons view while being examined 720. Current pupilometer examinations require forced medication dilation of the pupils that expose the patient to potential retinal damage from strong light 740. Current pupilometer examinations require a light stimulus to be projected onto the retina and/or surface of the eye exposing the patient to potential retinal and surface damage 760. Current pupilometer examinations are infrequent and do not provide continual or frequent pupillary assessments 750 of one embodiment.

Figure 8A:
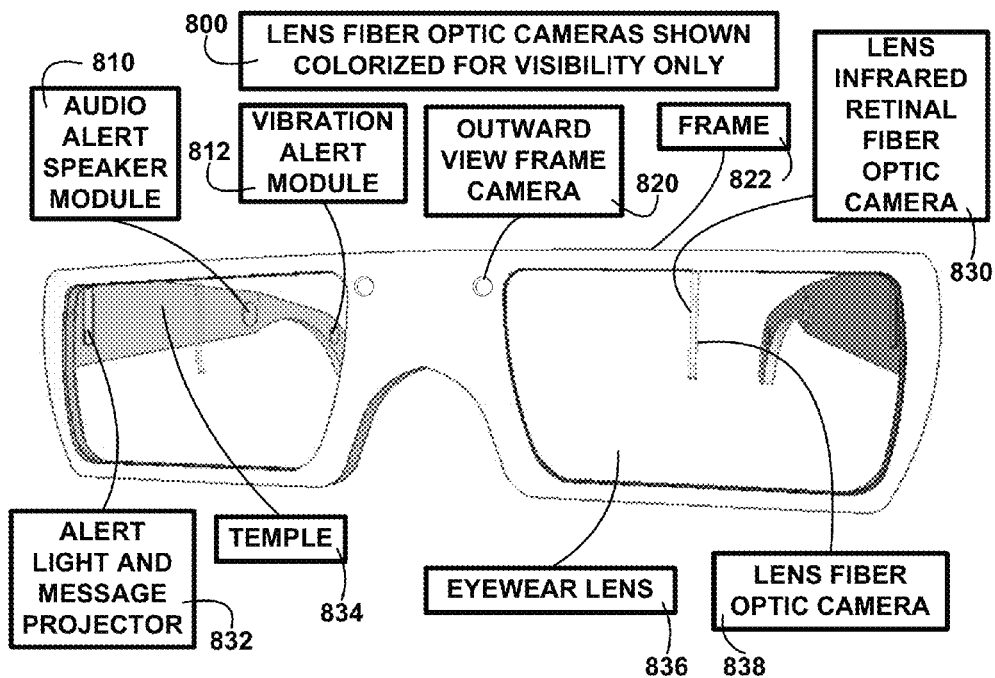
FIG. 8A shows for illustrative purposes only an example of a frame and lens fiber optic camera combination eyewear pupilometer of one embodiment.

Combination Eyewear Pupilometer:

FIG. 8A shows for illustrative purposes only an example of a frame and lens fiber optic camera combination eyewear pupilometer of one embodiment. FIG. 8A shows a frame 822 for vision wear, eyewear or pair of glasses. In one embodiment the eyewear pupilometer may include embedded into the eyewear lens 836 at least two lens fiber optic camera 838 modules, wherein at least one lens fiber optic camera 838 module is configured to include a lens with a focal length to focus on the exterior surfaces of the eye and wherein at least one lens fiber optic camera 838 module is configured to include a lens with a focal length to focus on the retina through the pupil, forming a lens infrared retinal fiber optic camera 830. The frame 822 includes at least one outward view frame camera 820 of one embodiment.

The frame is configured to include two temple pieces. Each of the temple 834 pieces may be configured to include an audio alert speaker module 810 in proximity to the ear, a vibration alert module 812 in proximity and in contact with the bones near the surface of the region above the ears to sense vibrations through the bone structure, and an alert light and message projector 832 to provide optic light flashes and readable text messages projected onto the inside surface of the eyewear lenses. The lens fiber optic cameras are shown colorized for visibility only 800 of one embodiment.

Figure 8B:
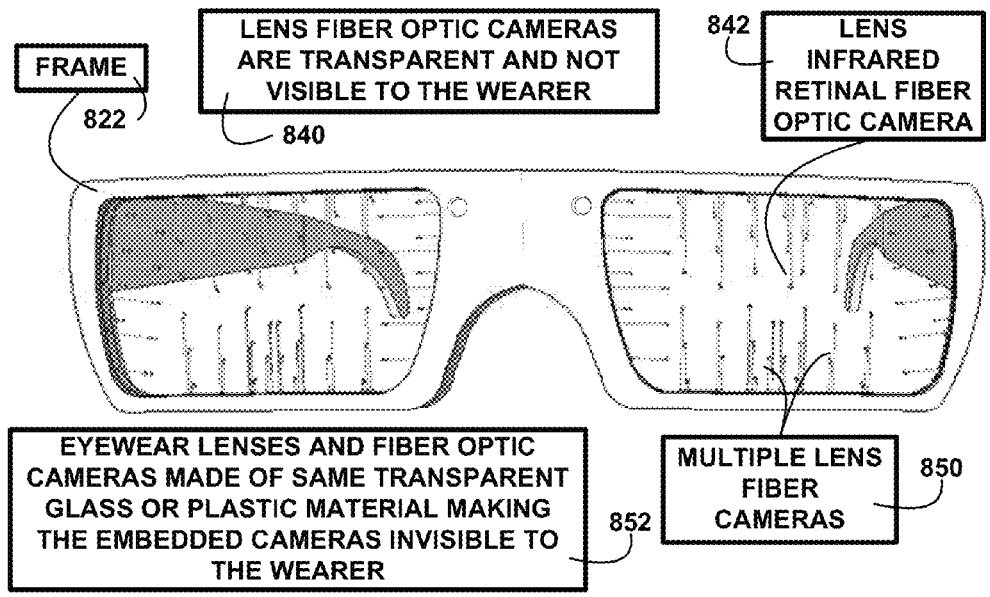
FIG. 8B shows for illustrative purposes only an example of a lens fiber optic camera eyewear pupilometer of one embodiment.

Lens Fiber Optic Camera Eyewear Pupilometer:

FIG. 8B shows for illustrative purposes only an example of a lens fiber optic camera eyewear pupilometer of one embodiment. FIG. 8B shows a frame 822 for vision wear, eyewear or pair of glasses. In one embodiment the eyewear pupilometer may include embedded into the eyewear lens 836 of FIG. 8A at least multiple lens fiber optic cameras 850 modules for example 59 fiber optic camera modules, wherein the plurality of fiber optic camera modules are configured to include a lens with a focal length to focus on the exterior surfaces of the eye and wherein at least one fiber optic camera module is configured to include a lens with a focal length to focus on the retina through the pupil, forming a lens infrared retinal fiber optic camera 842 of one embodiment.

Eyewear lenses and fiber optic cameras made of same transparent glass or plastic material making the embedded cameras invisible to the wearer 852. Lens fiber optic cameras are transparent and not visible to the wearer 840 of one embodiment.

Figure 8C:
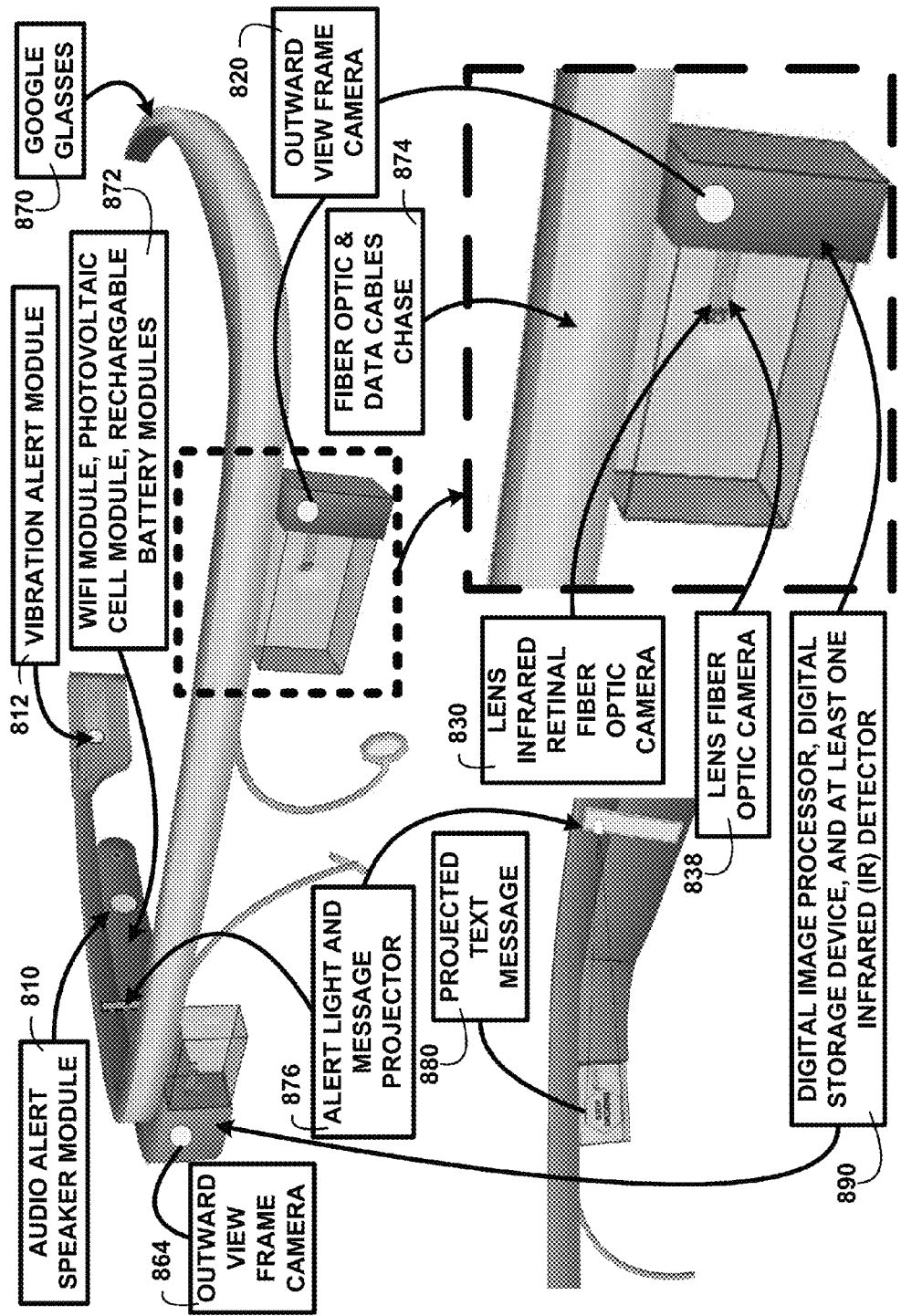
FIG. 8C shows for illustrative purposes only an example of a Google Glasses adapted for an eyewear pupilometer of one embodiment.

Google Glasses Eyewear Pupilometer:

FIG. 8C shows for illustrative purposes only an example of a Google Glasses adapted for an eyewear pupilometer of one embodiment. FIG. 8C shows a pair of Google Glasses 870 that are adapted using eyewear pupilometer features. The Google Glasses now include at least one lens infrared retinal fiber optic camera and at least one lens fiber optic camera embedded into the lenses. Also included is at least one outward view frame camera 820, a fiber optic & data cables chase 874 formed from the frame with fiber optic and data cables not shown on the interior of the chase, a WI-FI module, a photovoltaic cell module, rechargeable battery modules 872, digital image processor, digital storage device, and at least one infrared (IR) detector 890. Embedded in at least one temple piece are at least one audio alert speaker module 810, vibration alert module 812, and alert light and message projector 876 used to create a projected text message 880 for example "stop driving" onto the inside of the lens. At least one USB connector module, not shown, is included at the end of a temple piece of one embodiment.

Figure 9A:
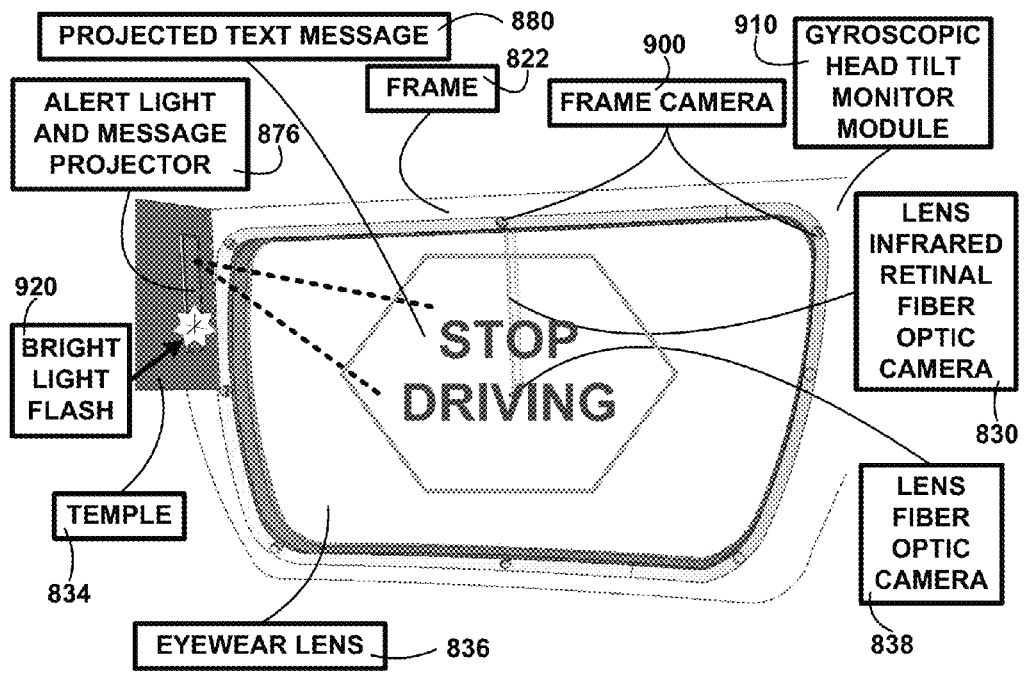
FIG. 9A shows for illustrative purposes only an example of frame fiber optic camera modules of one embodiment.

Frame Fiber Optic Camera Modules:

FIG. 9A shows for illustrative purposes only an example of frame fiber optic camera modules of one embodiment. FIG. 9A shows the eyewear frame 822 and eyewear lens 836. The eyewear lens includes at least one lens fiber optic camera 838 and at least one lens infrared retinal fiber optic camera 830. The eyewear frame includes a number of frame camera 900 modules, for example eight embedded into the frame material. Each of the frame camera 900 modules is recessed into the frame 822 to reduce extraneous light and is oriented in a direction to cover an overlapping region of the exterior eye surface of one embodiment.

The temple 834 is shown with the alert light and message projector 876. The light module is not used for pupilometer examination but to provide an optical stimulus for example a bright light flash 920 to awaken the driver and direct their attention to the projected text message 880 for example "wake up", "pull over", "stop driving" or other suitable message. A gyroscopic head tilt monitor module 910 is included in the frame to detect the driver's head tilted in a position for a period of time exceeding a predetermined period of time threshold wherein the time is in excess of a glance at for example a map. The gyroscopic head tilt monitor module may also be used to detect when a driver's is texting instead of looking ahead at the road of one embodiment.

Figure 9B:
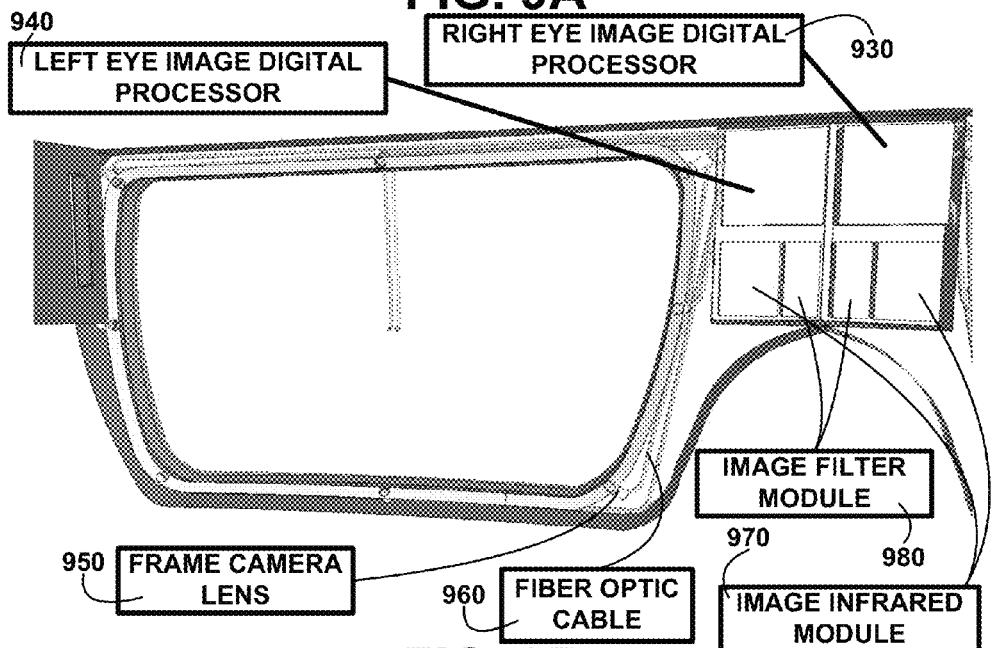
FIG. 9B shows for illustrative purposes only an example of frame embedded image processor modules of one embodiment.

Embedded Image Processor Modules:

FIG. 9B shows for illustrative purposes only an example of frame embedded image processor modules of one embodiment. FIG. 9B shows an exposed interior view of the eyewear pupilometer frame with components that were placed into position prior to molding the frame. The components include frame camera lens 950 and fiber optic cable 960 to transmit the captured image to a left eye image digital processor 940. The left eye image digital processor 940 may process the captured image through an image filter module 980 and/or an image infrared module 970 of one embodiment.

The image filter module 980 is used to apply various color filters to the image to create contrast between eye features for example the pupil and the iris. The image infrared module 970 is used to detect infrared wavelengths to create a visible digital image with eye features for example the pupil and iris with distinct contrast based on temperatures converted from the detected infrared wavelengths. Also shown are a right eye image digital processor 930, image filter module 980 and image infrared module 970 which are also embedded into a nose piece of the eyewear of one embodiment.

Eyewear pupilometer frame components are configured with left and right eye components to allow collection of images and sensor data for each eye independently. Separate pupillary assessments of each eye allow pre-diagnostic screening of each eye as ocular disease may occur in only one eye, and each eye is controlled by opposite sides of the brain and cranial features for example blood supplies. Separate pupillary assessments allow narrowing the area of potential problems affecting eye functions thereby speeding a full diagnostic evaluation and treatment of one embodiment.

Figure 10:
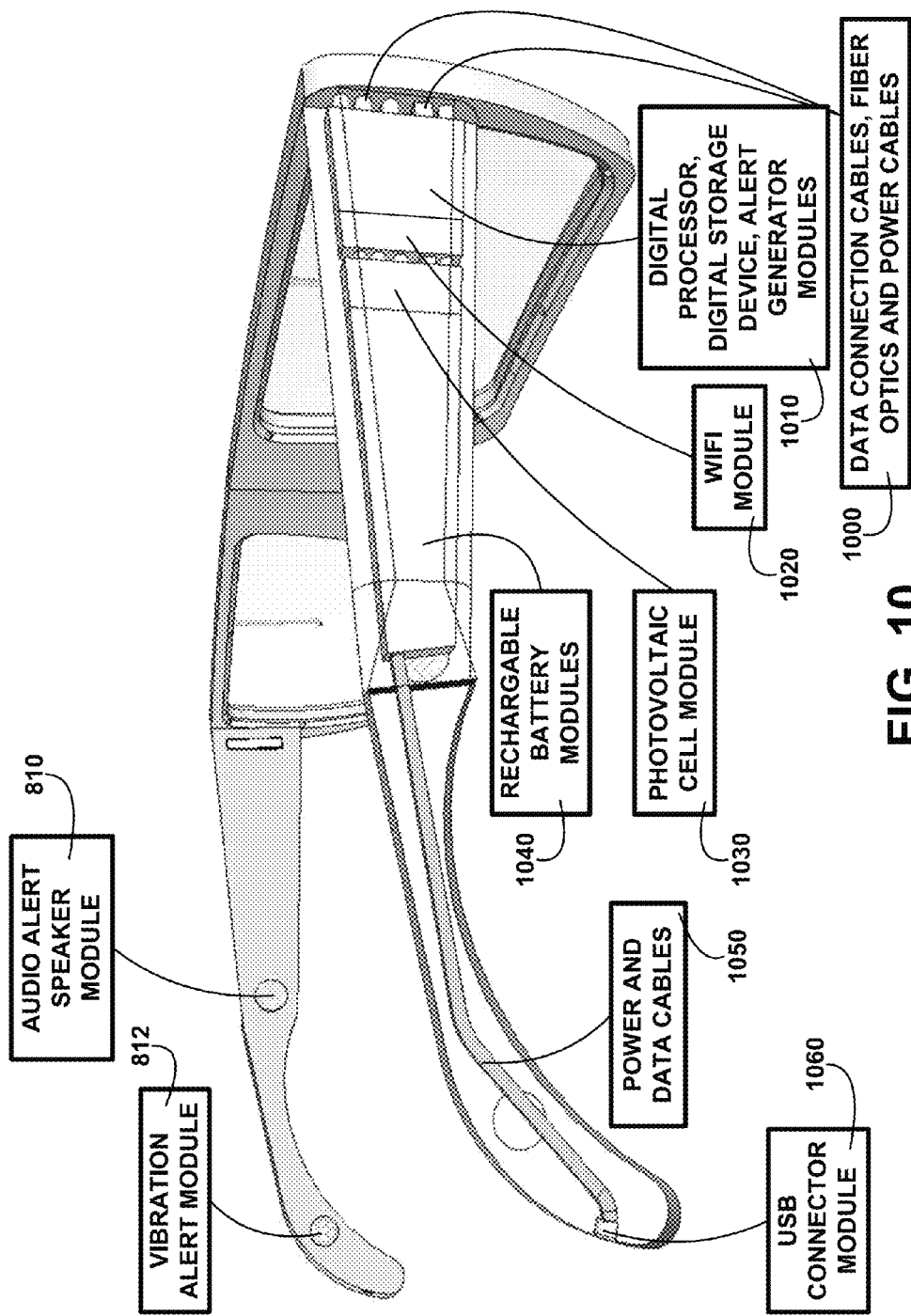
FIG. 10 shows for illustrative purposes only an example of temple embedded component modules of one embodiment.

Temple Embedded Component Modules:

FIG. 10 shows for illustrative purposes only an example of temple embedded component modules of one embodiment. FIG. 10 shows temple embedded component modules configured to include data connection cables, fiber optics and power cables 1000. Temple embedded components are configured to include a digital processor, digital storage device, alert generator modules 1010 and a WI-FI module 1020. In one embodiment the temple embedded component modules are configured to include rechargeable battery modules 1040, power and data cables 1050 and a USB connector module 1060. FIG. 10 shows a photovoltaic cell module 1030 used to covert light transmitted through the fiber optic cables into electricity to charge the rechargeable battery modules 1040. FIG. 10 shows on the inside of the opposite temple the audio alert speaker module 810 and vibration alert module 812. The temple embedded component modules are position in a molding prior to molding the eyewear temple piece of one embodiment.

Figure 11:
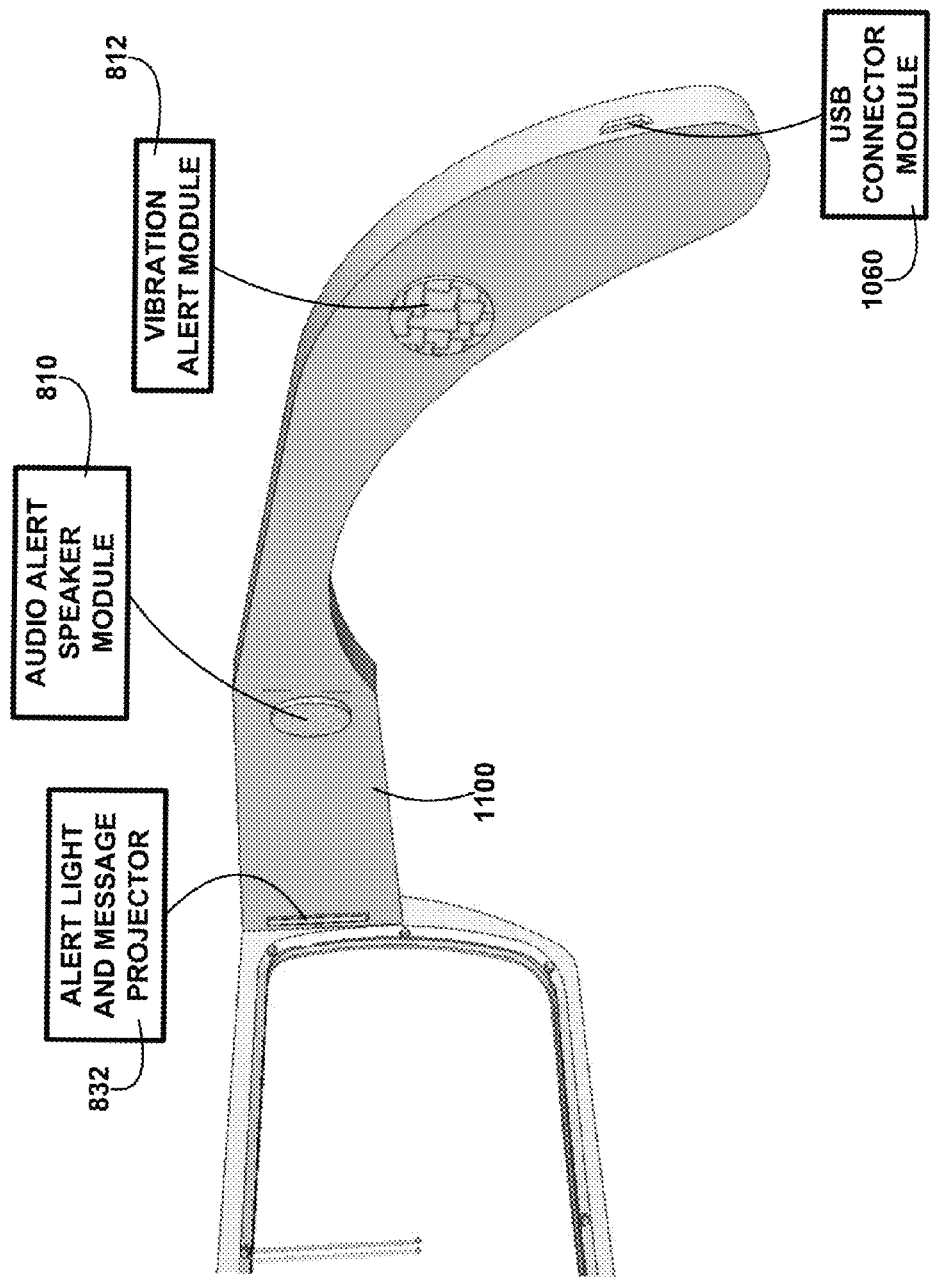
FIG. 11 shows for illustrative purposes only an example of driver alert modules of one embodiment.

Driver Alert Modules:

FIG. 11 shows for illustrative purposes only an example of driver alert modules of one embodiment. FIG. 11 shows driver alert modules including the alert light and message projector 832, audio alert speaker module 810 and vibration alert module 812. The USB connector module 1060 is located in proximity to the non-hinged terminus of the temple piece 1100 of one embodiment.

The driver alert modules for sending audio, projected messages and vibration alerts to the drowsy eyewear user. The audio alert speaker module 810 is configured for producing non-regular audio sounds and verbal messages from a speaker integrated into the eyewear frame temples in proximity to each ear, wherein the sounds are varied in pitch and volume and frequency of broadcast to not form a harmonic rhythm or lulling sensation. Audio messages may be used to read aloud projected text messages, simple "wake up", "pull over" and "stop driving" messages in varying volumes and tones to arouse the driver of one embodiment.

The alert light and message projector 832 is used for producing projected messages that are displayed onto the inside of the lenses including text messages that include "wake up", "pull over" and "stop driving", wherein the messages are varied in size, color and special effects including blinking, increasing light level or brightness, including bright flashes of light to arouse the driver of one embodiment.

The vibration alert module 812 is used for producing non-regular vibration alerts to the eyewear user to arouse the driver, that are transmitted from the eyewear frame temples in proximity to each ear boney areas, bridge of the nose through the frame nose piece, wherein the vibratory level, frequency and intensity are varied to not form a harmonic rhythm or lulling sensation of one embodiment.

The USB connector module 1060 is used for downloading a patient's pupillary images and sensor data using wired and wireless communication systems from the integrated digital database device into a patient's health records. The USB connector module 1060 is used for recharging the rechargeable battery modules 1040 of FIG. 10. An additional recharging device is an eyewear pupilometer charging platform wherein the eyewear is placed on the platform where power is induced into the batteries indirectly of one embodiment.

Figure 12:
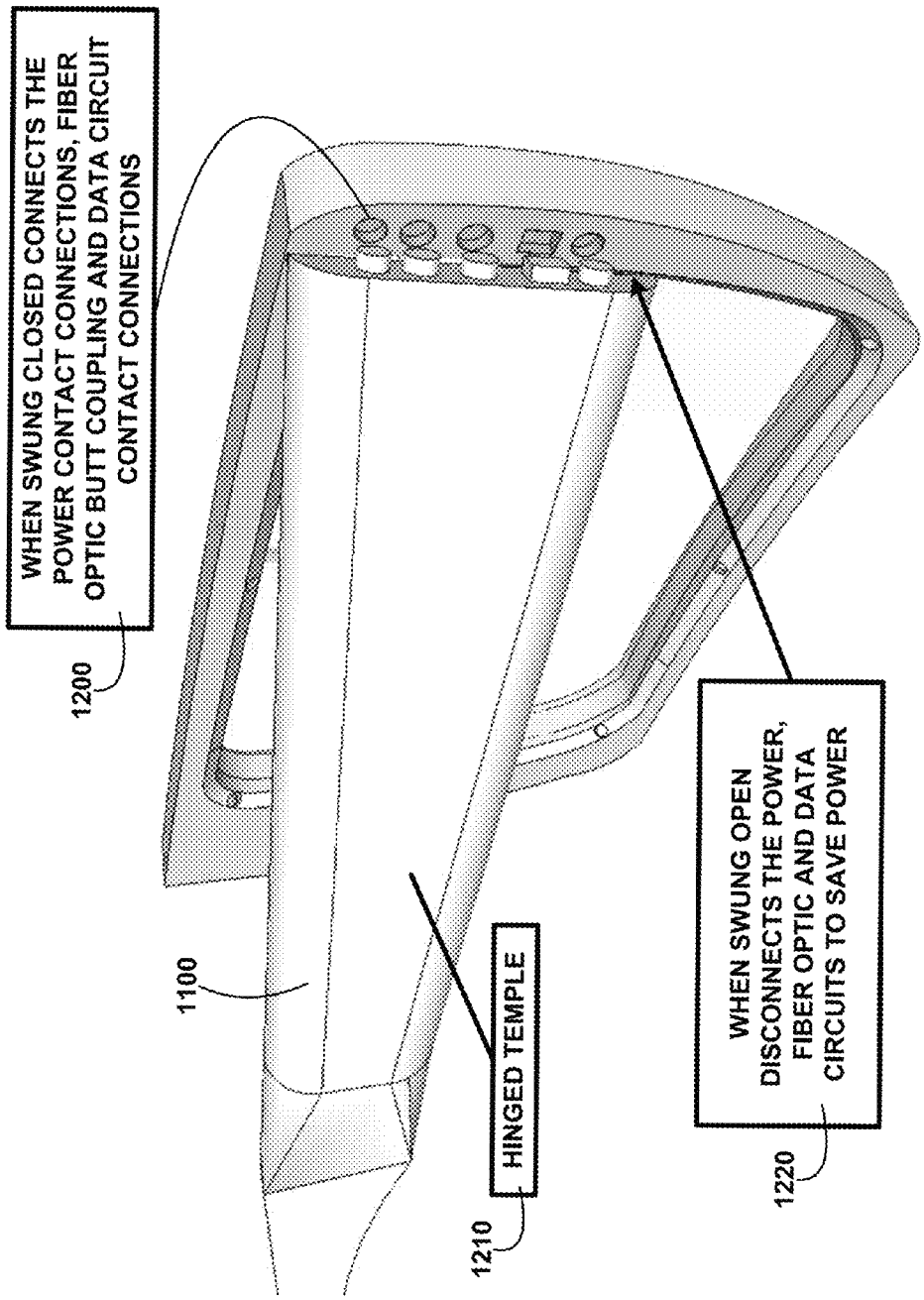
FIG. 12 shows for illustrative purposes only an example of hinged temple connections of one embodiment.

Hinged Temple Connections:

FIG. 12 shows for illustrative purposes only an example of hinged temple connections of one embodiment. FIG. 12 shows an eyewear pupilometer temple piece 1100 that is configured to include data connection cables, fiber optics and power cables extended outward from the hinged terminus of the temple. The eyewear frame is configured to include recessed connection receptacles for the extended data connection cables, fiber optics and power cables. The hinged temple 1210 can be swung open or closed. When swung closed connects the power contact connections, fiber optic butt couplings and data circuit contact connections 1200. Extended connectors seat into the recessed connection receptacles thereby completing the circuits and communication transmitting cables including fiber optic light transmitting cables and data transmitting cables. When swung open disconnects the power, fiber optic and data circuits to save power 1220. The extended connectors unseat and the cable connections are opened. This saves power stored in the rechargeable battery modules 1040 of FIG. 10 and stops operation of the eyewear pupilometer of one embodiment.

Pupilometer Security Features:

The orbital muscles include the ciliary muscles that control the iris constriction and dilation. Each individual has unique ciliary muscles, orbit size and shape, iris and other features that make their eye movements and pupillary constriction and dilation rates differ from others. These differences including iris pattern may be used in identification of an individual. For example when a person addresses and ATM to make a withdrawal from their banking account, after sliding their ATM card the ATM camera may take measurements of the persons eye movements and iris pattern to identify the individual from database data recorded and stored at the time of issuance of the ATM card. The eyewear pupilometer may be used to transmit a person's eye movements and iris pattern data to the ATM to perform the security check. This would ensure accurate data which may not be available from using the ATM camera due to the person wearing sunglasses or a hat. The same eyewear pupilometer eye movements and iris pattern data may be used in other security application in lieu placing your eye against a wall mounted scanner of one embodiment.

Pupilometer Remote Device Control Feature:

The eyewear pupilometer tracking of pupillary movements may also be used to control remote devices through the use of WI-FI communication modules. Eye movements may be calibrated with control or access features of the remote device to allow the wearer to coordinate pupillary movements to select and activate the control of access features of the remote device by transmitting the direction of the wearer is looking to correlate with the location of the remote device feature. An image of the remote device feature can be stored in the eyewear pupilometer and when the gaze of the wearer encounters an image matching the image of the remote device feature a series of optical movements for example a series of blinks for example three rapid blinks to activate the remote device feature. For example in a vehicle instead of taking a hand off of the steering wheel the driver can look at the radio to turn it on or adjust the volume or station. A predetermined eye movement for example an upward look can increase the volume or a downward view to lower volume. Side eye movements may be used to cycle radio station selections or activate a station scan or seek feature of the radio. This same feature can be used in other applications to operate other devices of one embodiment.

Figure 13:
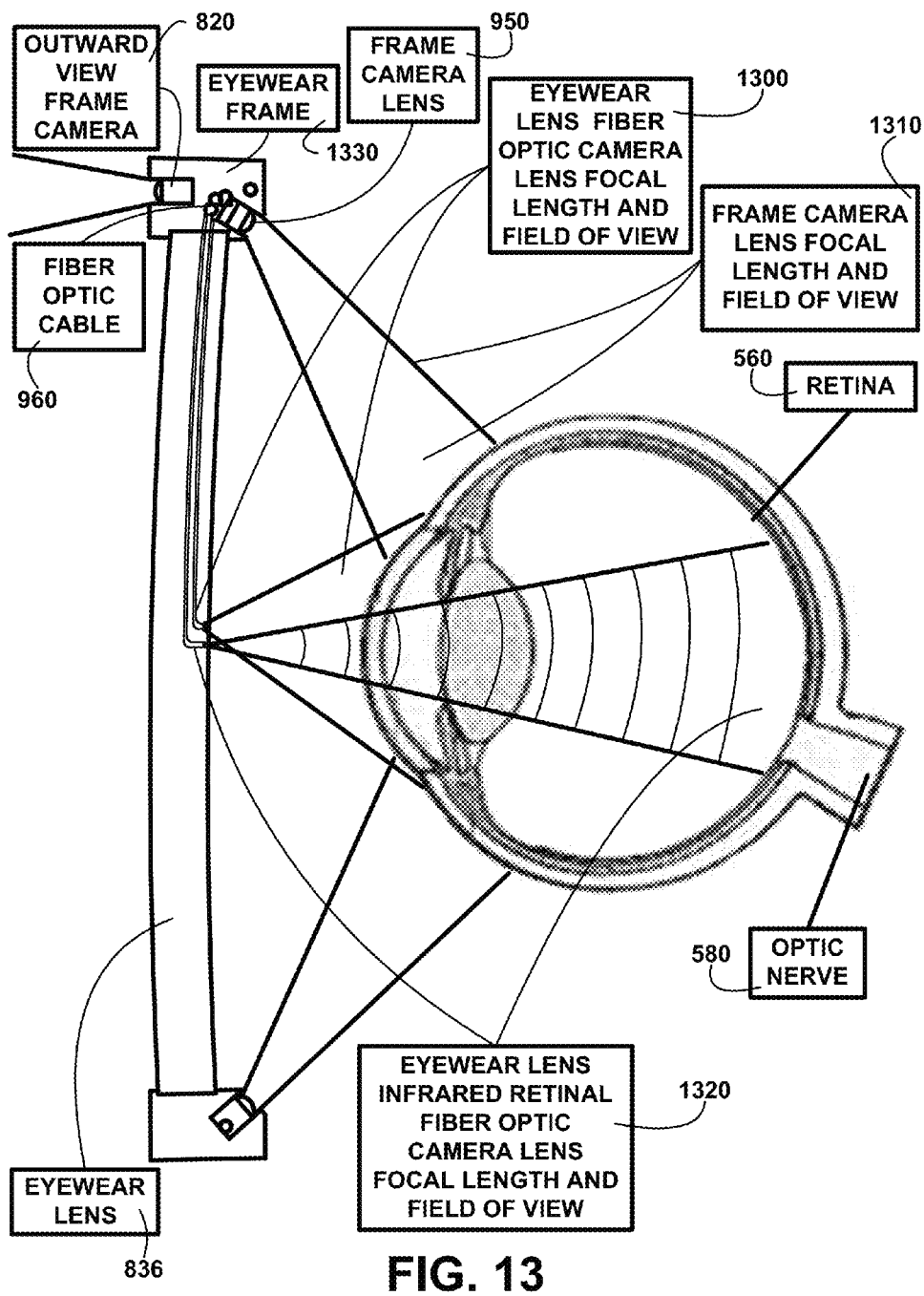
FIG. 13 shows for illustrative purposes only an example of eyewear camera focal lengths and field of views in a cross section view of one embodiment.

Camera Focal Lengths:

FIG. 13 shows for illustrative purposes only an example of eyewear camera focal lengths and field of views in a cross section view of one embodiment. FIG. 13 shows a cross sectional view of the eyewear pupilometer eyewear frame 1330 and eyewear lens 836. An eyewear lens infrared retinal fiber optic camera lens focal length and field of view 1320 focuses on the optic nerve 560 and retina 560. The eyewear lens infrared retinal fiber optic camera is embedded into the eyewear lens. Embedded in the eyewear frame 1330 are frame camera lens 950 modules. An eyewear lens fiber optic camera lens focal length and field of view 1300 is focused on the exterior surface of the eye. The images captured are transmitted through a fiber optic cable 960 embedded in the frame. An outward view frame camera 820 captures images of what is in the field of view of the user whether they are wide awake or asleep. The outward view frame camera 820 may be used to capture video of the vehicle movements and may provide a record of an accident of one embodiment.

Figure 14:
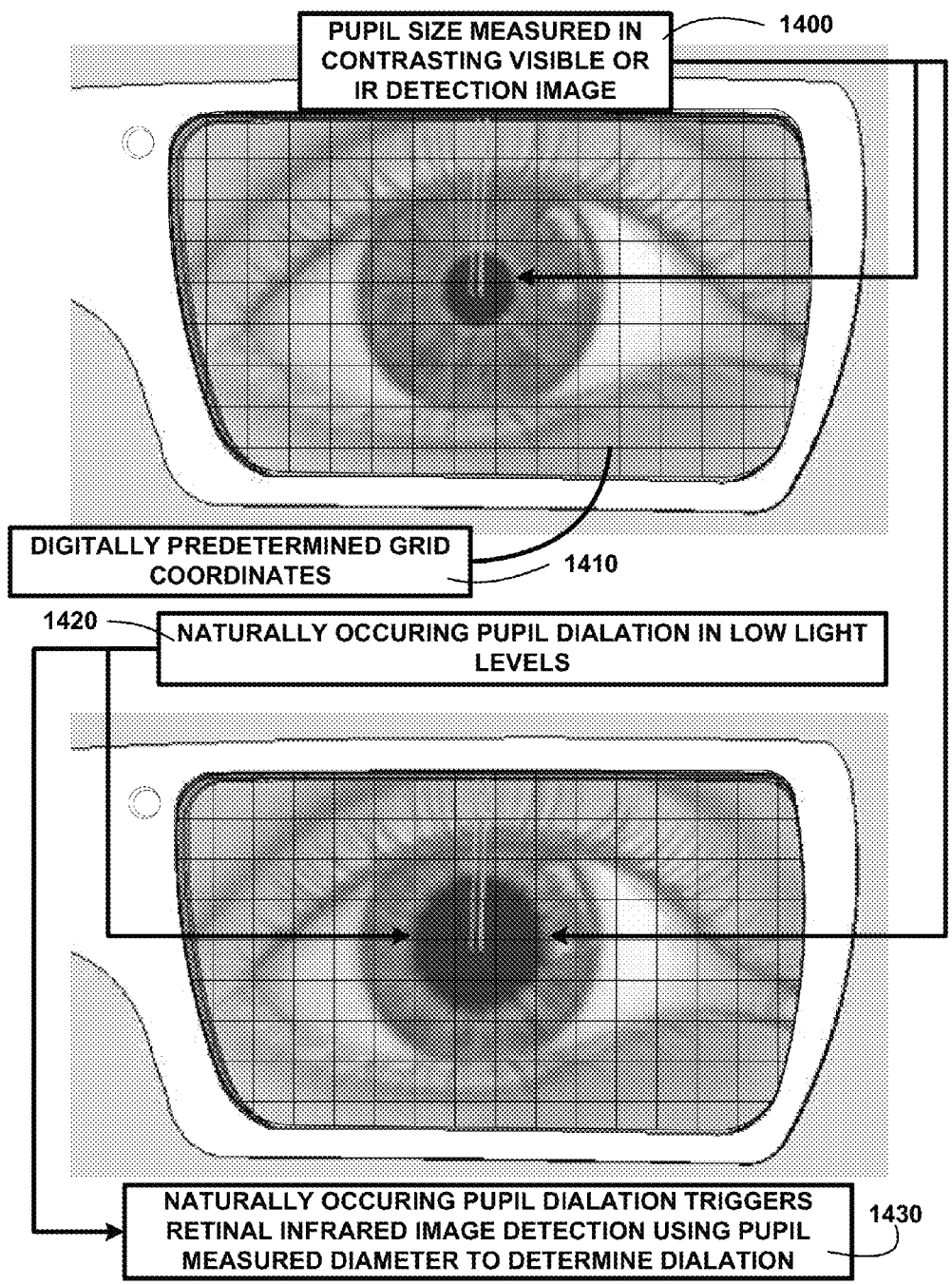
FIG. 14 shows for illustrative purposes only an example of pupil size measurements of one embodiment.

Pupil Size Measurements:

FIG. 14 shows for illustrative purposes only an example of pupil size measurements of one embodiment. FIG. 14 shows digitally predetermined grid coordinates 1410 created in digital processors used for analyzing pupillary and retinal images and sensor data. Pupil size measured in contrasting visible or infrared (IR) detection image 1400 can be used to determine whether the pupil is dilated or not. Naturally occurring pupil dilation in low light levels 1420 is frequent during the hours of the day. Naturally occurring pupil dilation triggers retinal infrared image detection using pupil measured diameter to determine dilation 1430 of one embodiment.

Figure 15A:
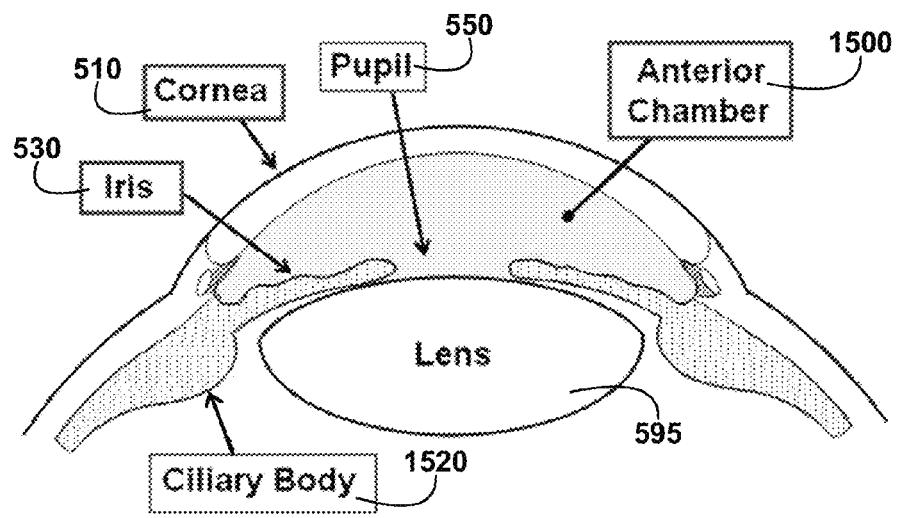
FIG. 15A shows for illustrative purposes only an example of a cross section view of the pupil opening structure of one embodiment.

Pupil Opening Structure:

FIG. 15A shows for illustrative purposes only an example of a cross section view of the pupil opening structure of one embodiment. FIG. 15A shows the structure of the front of an eye including the cornea 510, anterior chamber 1500, iris 530, pupil 550, lens 595 and ciliary body 1520. The pupil opening allows capturing an image of the retina of one embodiment.

Figure 15B:
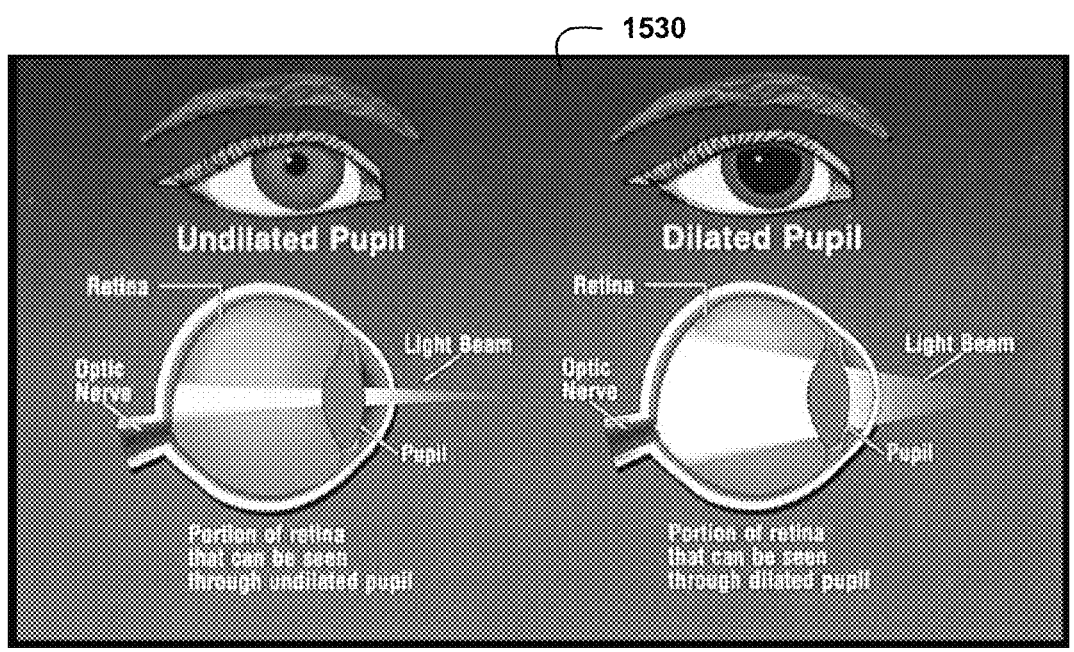
FIG. 15B shows for illustrative purposes only an example of retinal views through pupil openings of one embodiment.

Retinal Views Through Pupil Openings:

FIG. 15B shows for illustrative purposes only an example of retinal views through pupil openings of one embodiment. FIG. 15B shows an undilated pupil chart 1530 where a light beam passing through the smaller opening of the pupil or infrared wavelengths passing from the retina and optic nerve provide a smaller image of the retinal region in the interior of the eye. A dilated pupil allows a larger light beam to pass through the larger pupil opening or wider retinal area infrared wavelengths can pass out through the larger pupil opening allowing capture of an image of the wider retinal area of one embodiment.

Figure 16:
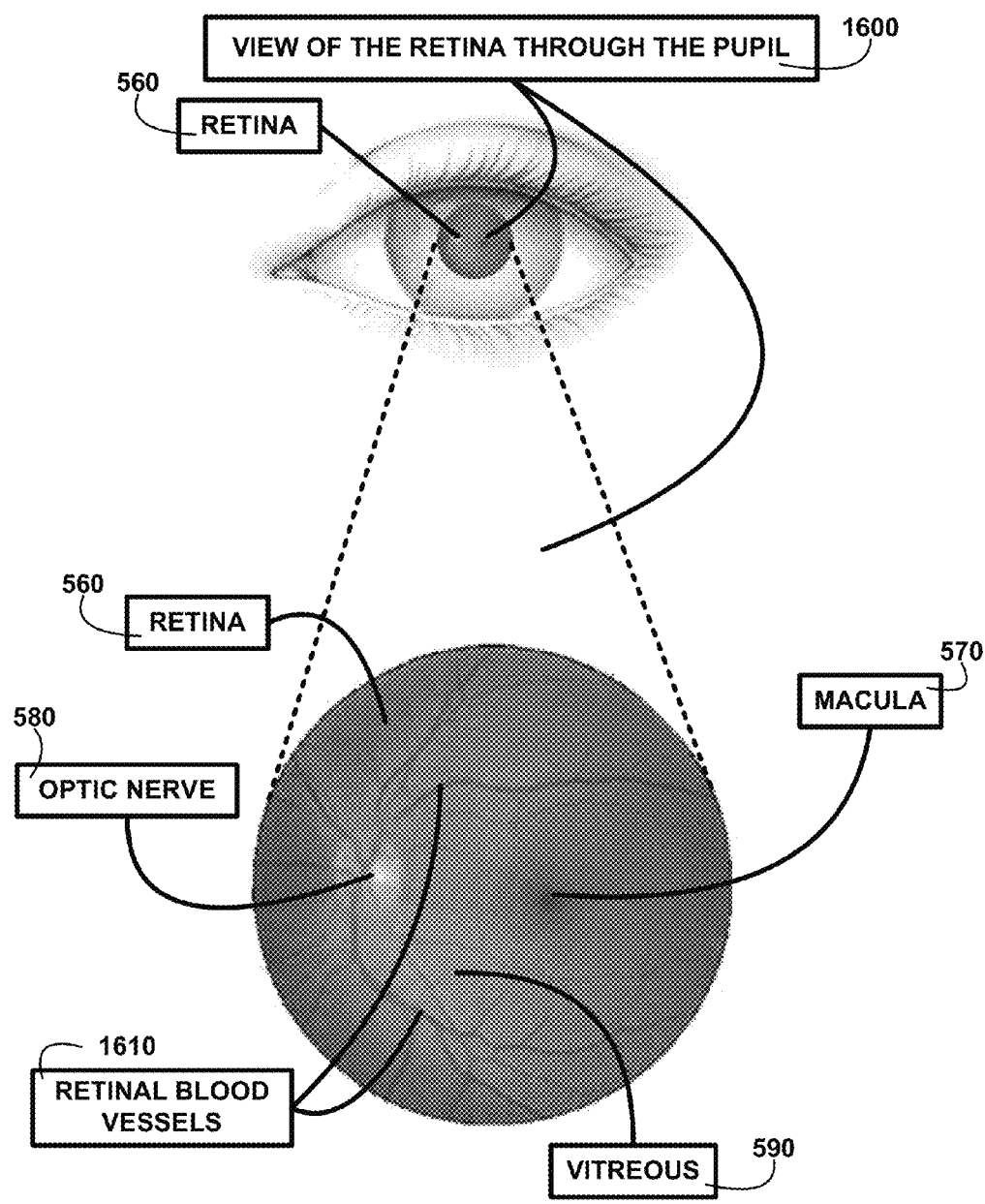
FIG. 16 shows for illustrative purposes only an example of a retinal image capture of infrared wavelengths passing through a dilated pupil of one embodiment.

Retinal Image Capture:

FIG. 16 shows for illustrative purposes only an example of a retinal image capture of infrared wavelengths passing through a dilated pupil of one embodiment. FIG. 16 shows a view of the retina through the pupil 1600. The retina 560 area is dark due to the limited amount of light entering through the pupil of one embodiment.

Conventional retinal scans project bright light and/or an infrared light source into the retinal area in order to capture images. The project of a light source into the retinal area may damage retinal tissues of one embodiment.

The eyewear pupilometer does not project a light source into the retinal area. It detects infrared light emanating from the retinal area from the heat levels associated with the retinal features for example the optic nerve 580, macula 570, retinal blood vessels 1610 and vitreous 590. The eyewear pupilometer infrared detectors are sensors that measure the infrared wavelengths. The wavelengths vary with the temperatures of the retinal features. The images captured using the IR detectors contrast the retinal features making them distinguishable. The IR detector images form a thermal image of the features. The thermal images allow determination of blood vessels temperatures which using algorithms to determine blood temperatures used in monitoring body temperatures. The IR wavelengths associated with the retinal blood vessels are also used to determine oxygen levels in the blood flows as the concentrations of oxygen in the blood vary the temperatures. The eyewear pupilometer may capture IR images of the retinal area including blood vessels on a continual basis for a period of time which when processed for size and temperature may be used to determine a pulse rate of one embodiment.

Figure 17A:
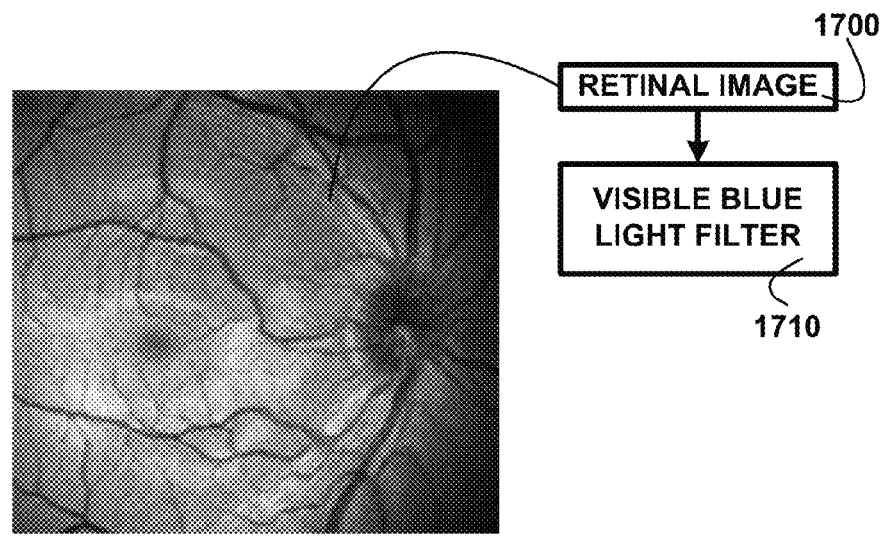
FIG. 17A shows for illustrative purposes only an example of a blue filtered retinal image of one embodiment.

Blue Filtered Retinal Image:

FIG. 17A shows for illustrative purposes only an example of a blue filtered retinal image of one embodiment. FIG. 17A shows the contrast in a retinal image 1700 captured in visible light projected onto the retina. Due to the redness of the natural coloring a visible blue light filter 1710 dampens the red values producing a higher contract of the retinal features of one embodiment.

Figure 17B:
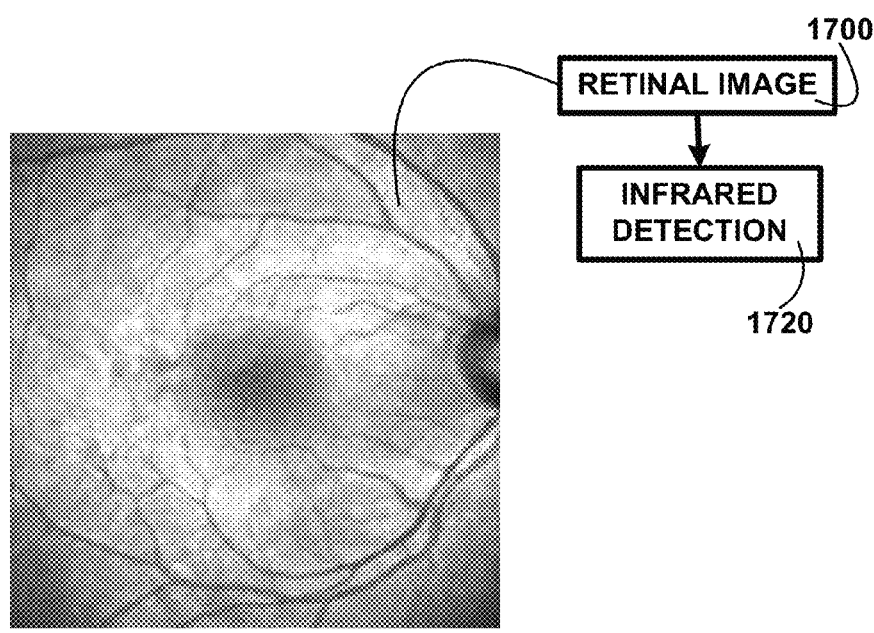
FIG. 17B shows for illustrative purposes only an example of an infrared detected retinal image of one embodiment.

Infrared Detected Retinal Image:

FIG. 17B shows for illustrative purposes only an example of an infrared detected retinal image of one embodiment. FIG. 17B shows a retinal image 1700 captured by the eyewear pupilometer and processed using infrared detection 1720. The images both produce high contrast of the retinal features, however the eyewear pupilometer does so without projecting potentially damaging light into the eye of one embodiment.

Figure 18:
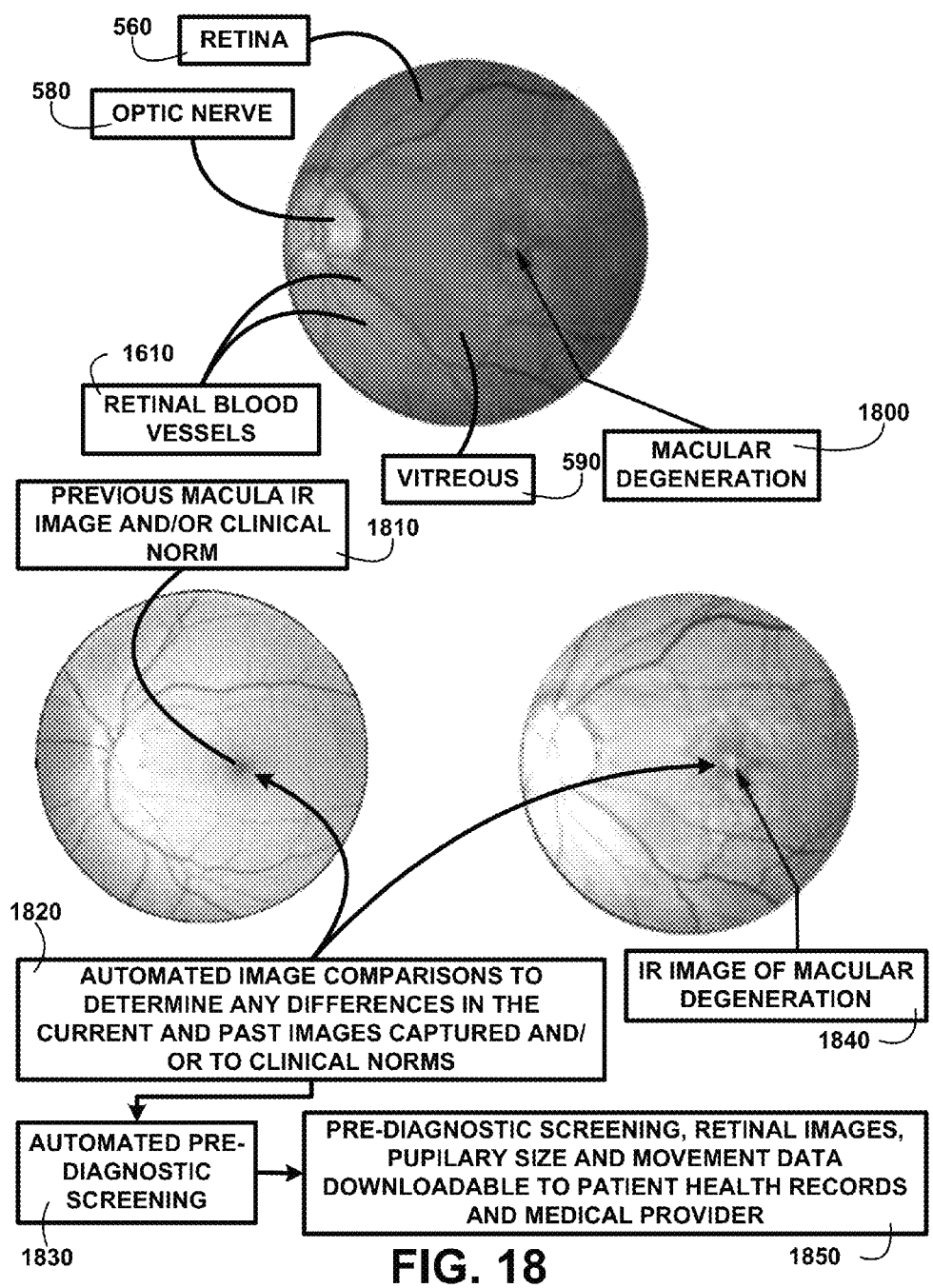
FIG. 18 shows for illustrative purposes only an example of automated pre-diagnostic screening of one embodiment.

Automated Pre-Diagnostic Screening:

FIG. 18 shows for illustrative purposes only an example of automated pre-diagnostic screening of one embodiment. FIG. 18 shows a retinal image captured with projected visible light into the eye. The visible light image shows the optic nerve 580, retina 560, and retinal blood vessels 1610, vitreous 590 and macular degeneration 1800. The eyewear pupilometer performs frequent image captures including a number of images per minute, hour, day and over periods of weeks and months provides numerous before and after images for observing changes in the retina. The eyewear pupilometer performs automated image comparisons to determine any differences in the current and past images captured and/or to clinical norms 1820. A previous macula IR image and/or clinical norm 1810 may be compared to a current IR image of macular degeneration 1840. Automated pre-diagnostic screening 1830 performed frequently allows changes including initiation of macular degeneration to be discovered much earlier and alerts the eyewear user and their medical provider to begin treatment much sooner. Pre-diagnostic screening, retinal images, pupillary size and movement data downloadable to patient health records and medical provider 1850 of one embodiment.

Figure 19:
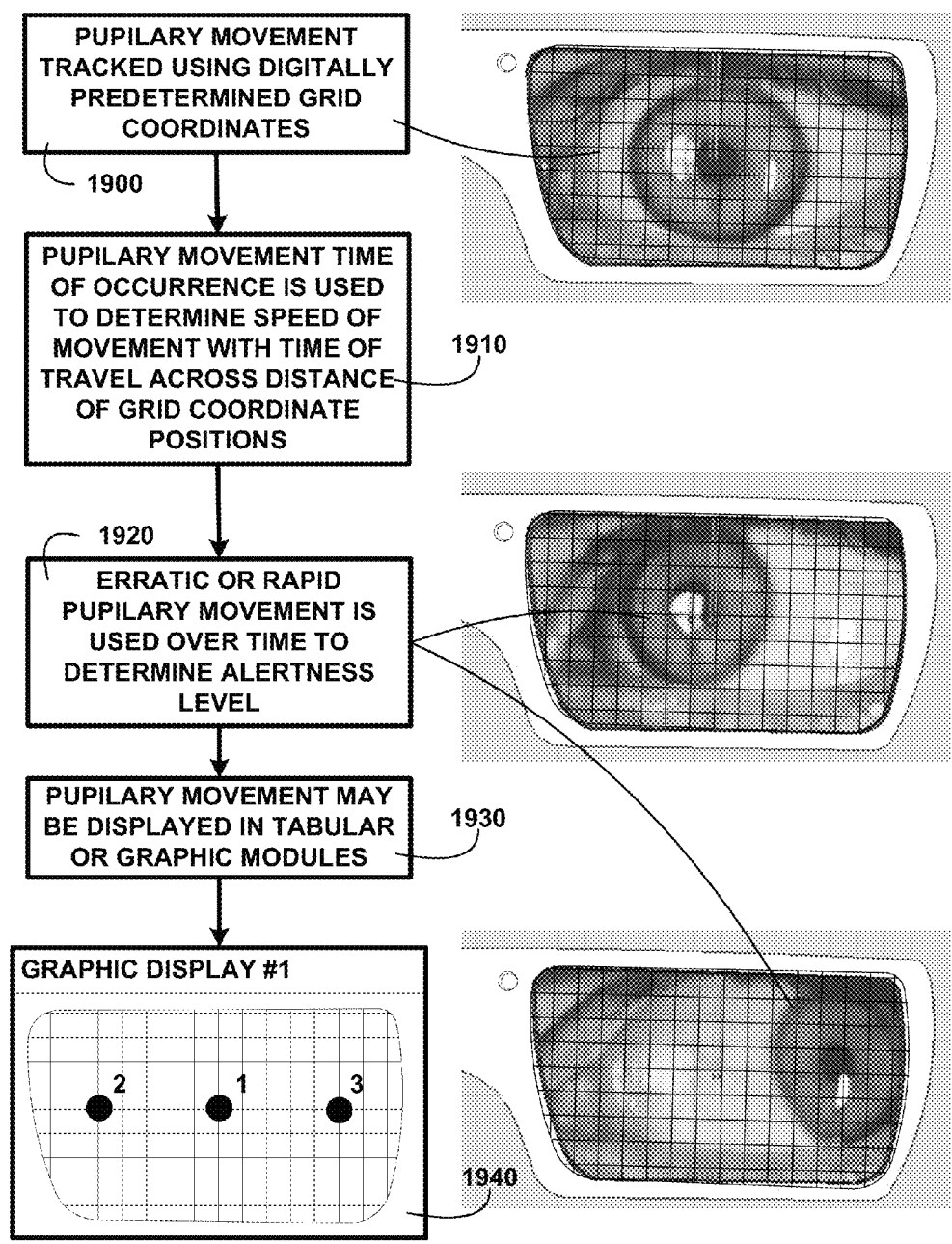
FIG. 19 shows for illustrative purposes only an example of pupillary movement tracking of one embodiment.

Pupillary Movement Tracking:

FIG. 19 shows for illustrative purposes only an example of pupillary movement tracking of one embodiment. FIG. 19 shows pupillary movement tracked using digitally predetermined grid coordinates 1900. Pupillary movement time of occurrence is used to determine speed of movement with time of travel across distance of grid coordinate positions 1910. Erratic or rapid pupillary movement is used over time to determine alertness level 1920 of the wearer for example a driver. Pupillary movement may be displayed in tabular or graphic modules 1930 when the data is viewed in the wearer patient health records. A graphic display #1 1940 show a plotting of the pupil positions over a specific period of time and may facilitate a medical provider's evaluation of the data of one embodiment.

The eyewear pupilometer automatically determines and analysis of the pupil movements and compares the results with normal thresholds to make an assessment of for example a driver's awareness and alertness levels. The normal thresholds may be determined from actual pupillary movements of the wearer over a period of time in which the total data analyzed is during a period when the wearer is wide awake. Customizing of the thresholds provides a more accurate assessment over study result thresholds from a large group who may or may not share the same physiology, sleep patterns, job schedules or even places of residence for example a person living in Alaska or northern Canada where daylight hours vary dramatically with those of more southern latitudes of one embodiment.

Figure 20:
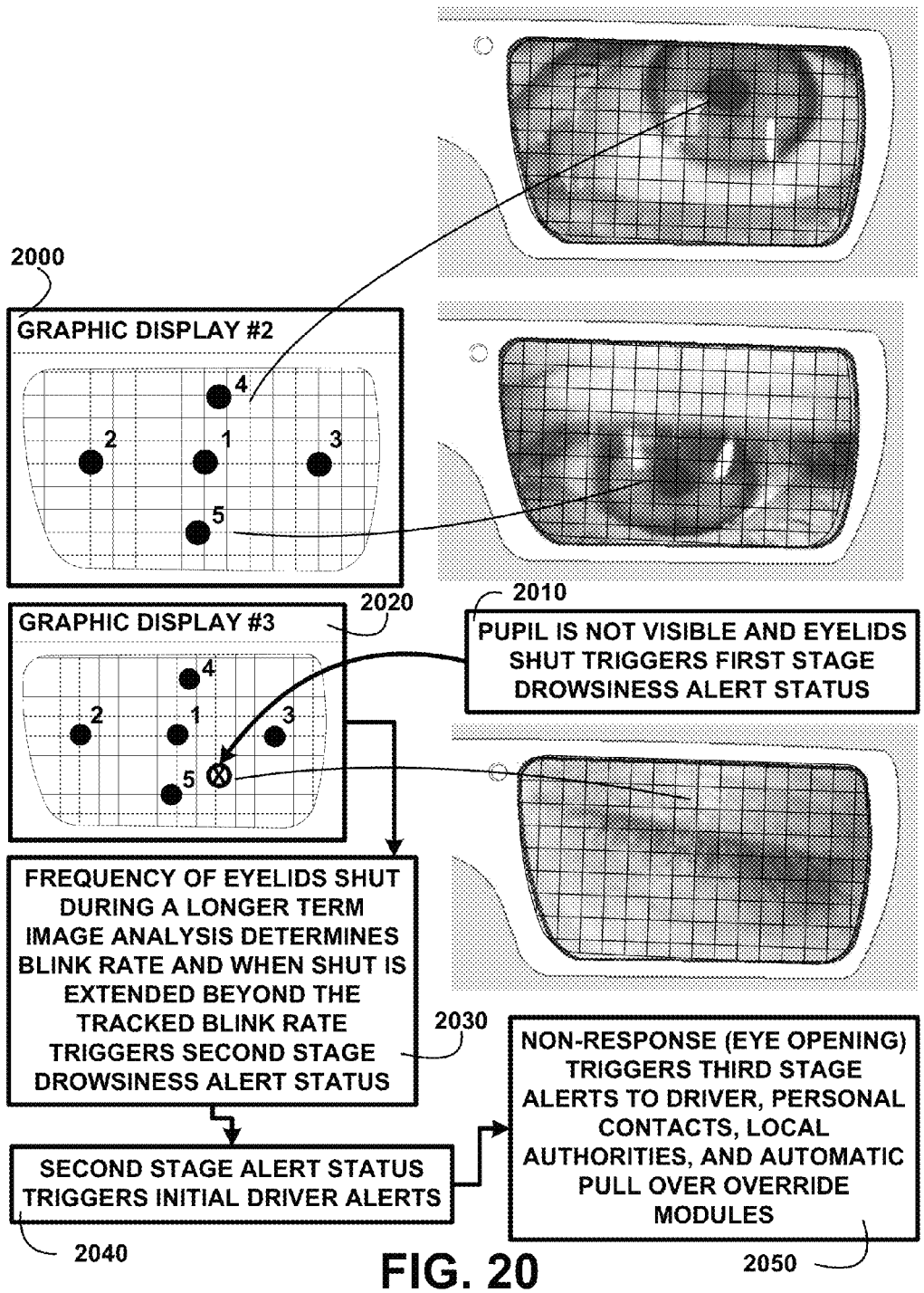
FIG. 20 shows for illustrative purposes only an example of pupillary movement drowsiness determination of one embodiment.

Pupillary Movement Drowsiness Determination:

FIG. 20 shows for illustrative purposes only an example of pupillary movement drowsiness determination of one embodiment. FIG. 20 shows a continuing graphic display #2 2000 of the wearer's pupil movements. If the analysis of the pupil size and movements are undiscernible this may indicate the eyelids are shut. Determination that the pupil is not visible and eyelids shut triggers first stage drowsiness alert status 2010. Frequency of eyelids shut during a longer term image analysis determines blink rate and when shut is extended beyond the tracked blink rate triggers second stage drowsiness alert status 2030. A second stage alert status triggers initial driver alerts 2040. Graphic display #3 2020 shows a non-response (eye not opening), Non-response (eye opening) shown in triggers third stage alerts to driver, personal contacts, local authorities, and automatic pull over override modules 2050 activation of one embodiment.

Figure 21:
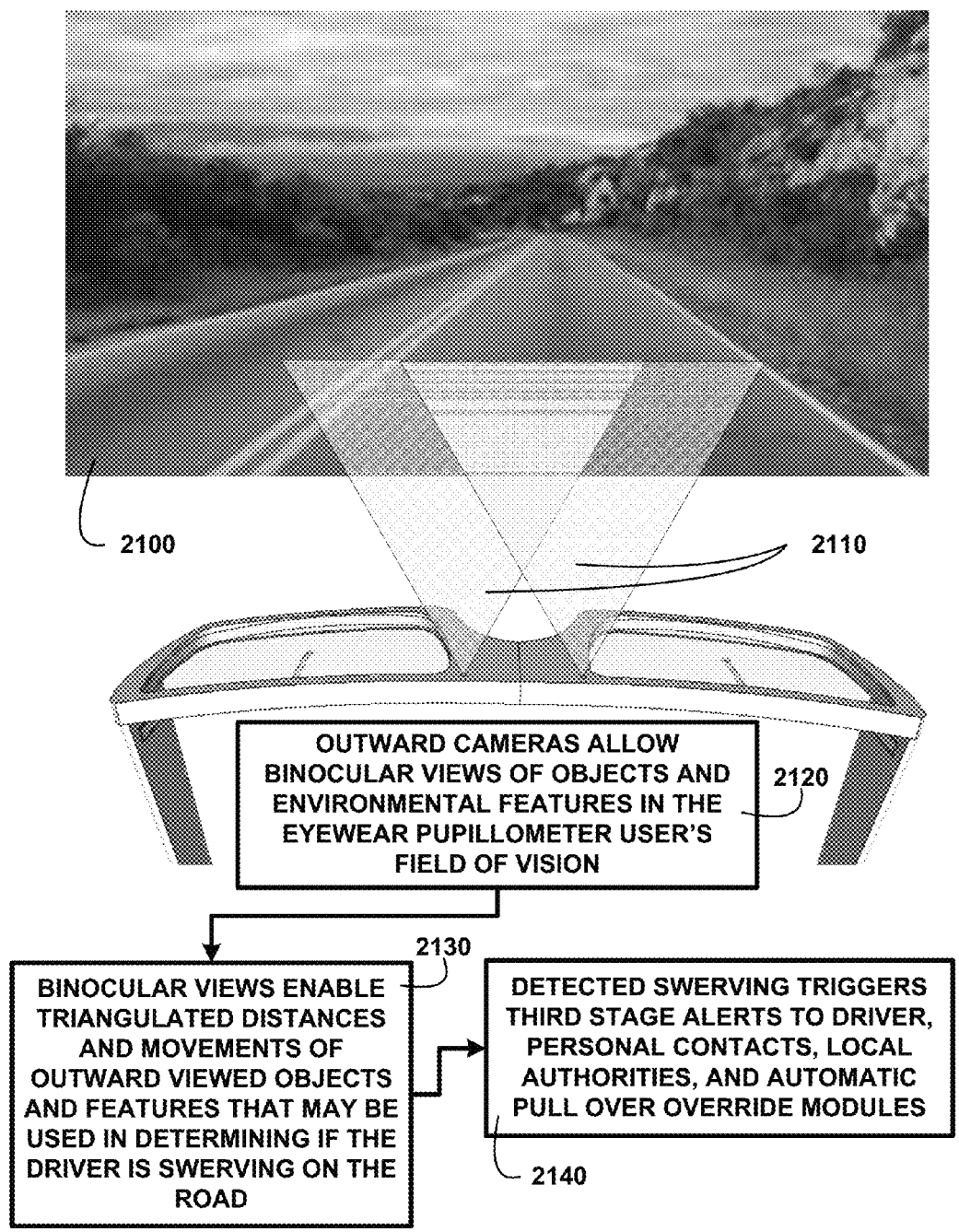
FIG. 21 shows for illustrative purposes only an example of outward camera image analysis of one embodiment.

Outward Camera Image Analysis:

FIG. 21 shows for illustrative purposes only an example of outward camera image analysis of one embodiment. FIG. 21 shows outward camera fields of vision 2110 in the direction the wearer is facing 2100. The eyewear pupilometer is configured with two outward cameras. Two outward cameras allow binocular views of objects and environmental features in the eyewear pupilometer user's field of vision 2120. Binocular views enable triangulated distances and movements of outward viewed objects and features that may be used in determining if the driver is swerving on the road 2130. Detected swerving triggers third stage alerts to driver, personal contacts, local authorities, and automatic pull over override modules 2140 activation of one embodiment.

Figure 22A:
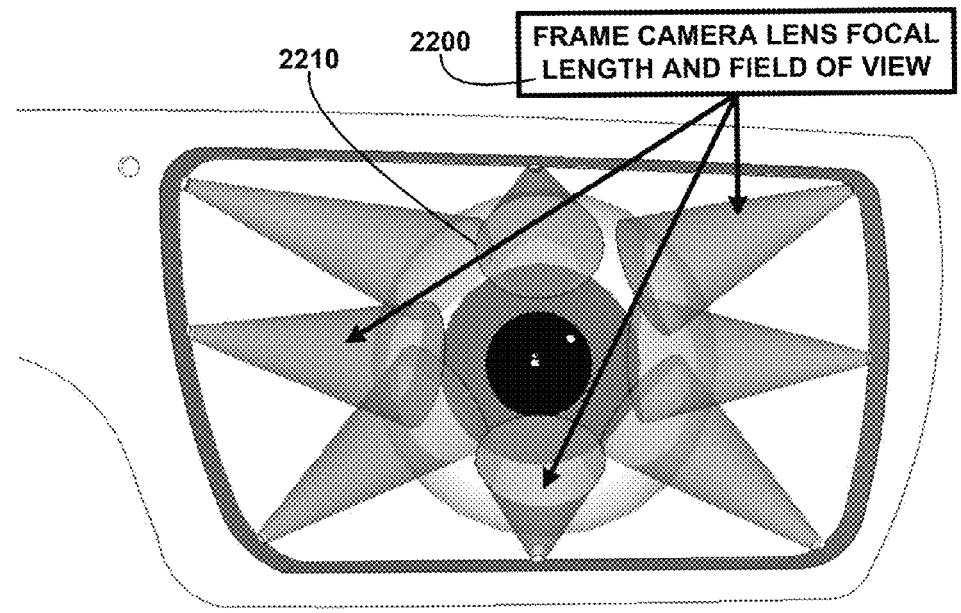
FIG. 22A shows for illustrative purposes only an example of frame camera field of view of one embodiment.

Frame Camera Field of View:

FIG. 22A shows for illustrative purposes only an example of frame camera field of view of one embodiment. FIG. 22A shows frame camera lens focal length and field of view 2200 from the position around the inside perimeter of the frame.

The frame cameras fields of view overlap 2210 the area surrounding the iris and pupil when the eye is looking forward of one embodiment.

Figure 22B:
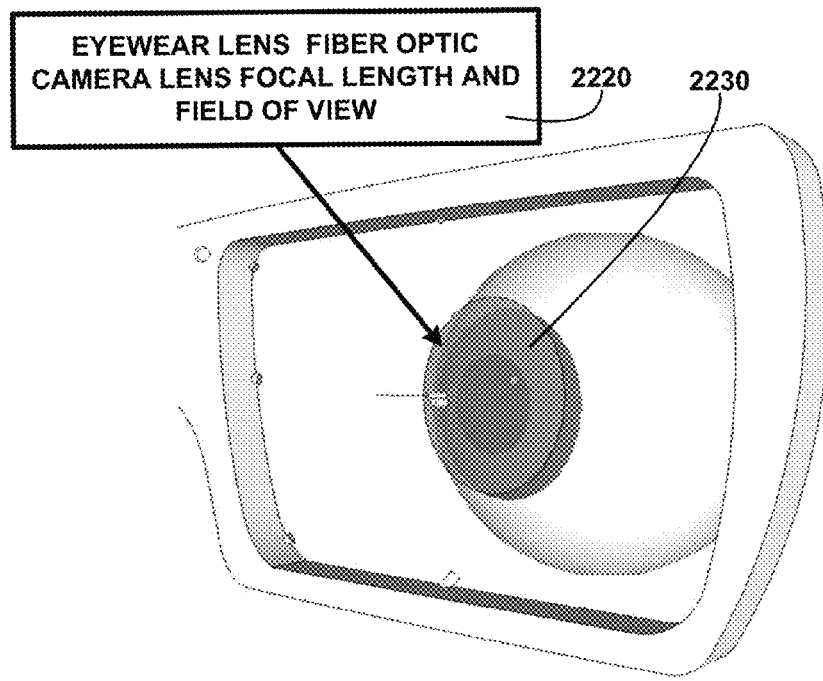
FIG. 22B shows for illustrative purposes only an example of eyewear lens embedded fiber optic camera field of view of one embodiment.

Eyewear Lens Fiber Optic Camera Field of View:

FIG. 22B shows for illustrative purposes only an example of eyewear lens embedded fiber optic camera field of view of one embodiment. FIG. 22B shows eyewear lens fiber optic camera lens focal length and field of view 2220. The eyewear lens fiber optic camera lens field of view covers the iris and pupil area 2230 when the eye is looking forward. As the eye is moving left, right, up and down the combined fields of view of the frame cameras and lens camera create a mosaic of the exposed surface area of the eye of one embodiment.

Frame cameras can capture a clear view of the pupil when looking other than forward. The mosaic overlapping of images captured of the pupil allow accurate and continual assessment of pupil size and movement. The analysis using the center of the detected pupil to assign a grid coordinate used in plotting and noting movement frequency and speed of one embodiment.

Figure 23:
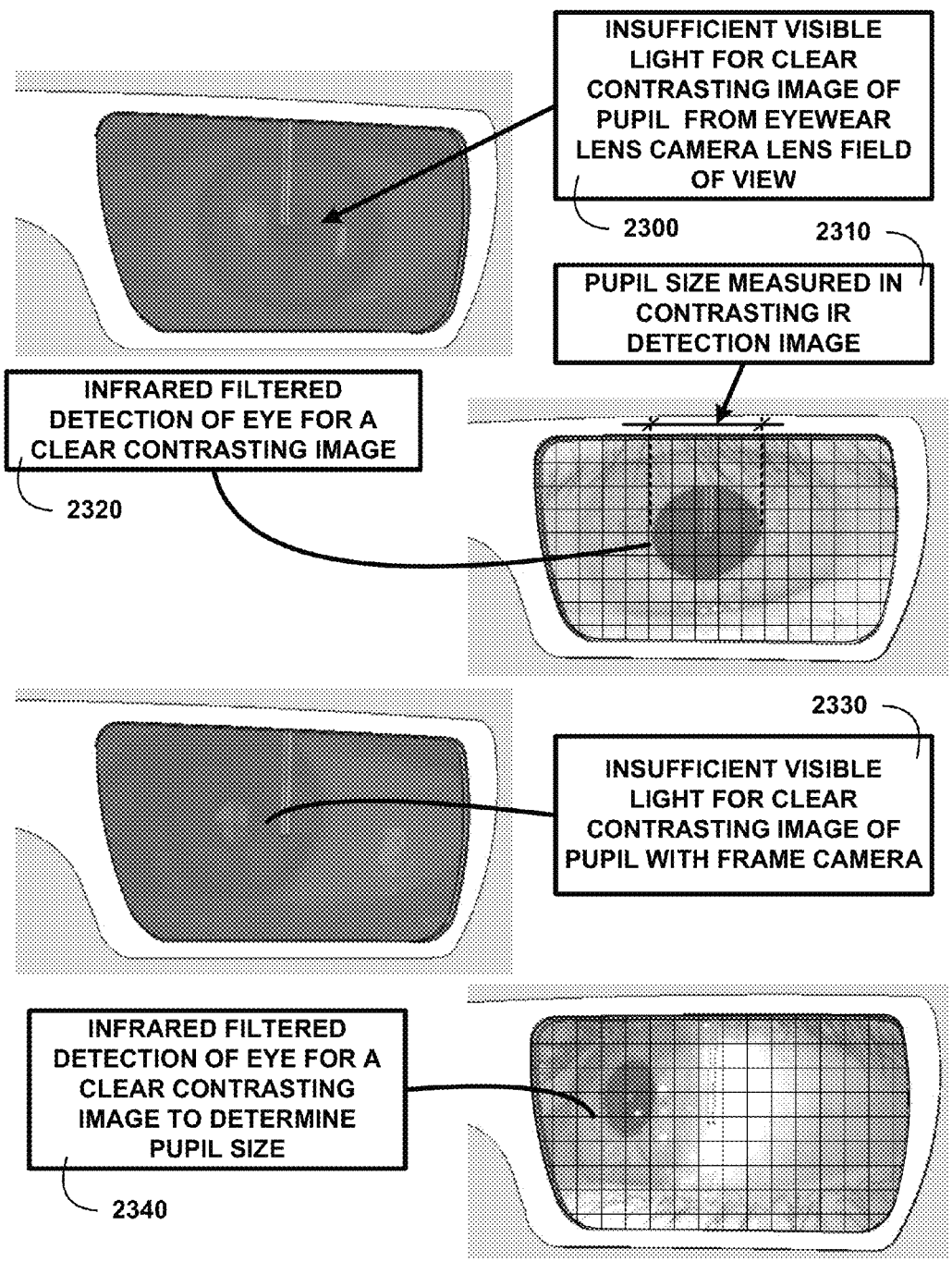
FIG. 23 shows for illustrative purposes only an example of pupil measurement in low light of one embodiment.

Pupil Measurement in Low Light:

FIG. 23 shows for illustrative purposes only an example of pupil measurement in low light of one embodiment. FIG. 23 shows insufficient visible light for clear contrasting image of pupil from eyewear lens camera lens field of view 2300. The low light captured image is automatically processed through the infrared detector. IR processing using infrared filtered detection of eye for a clear contrasting image 2320. Pupil size measured in contrasting IR detection image 2310 can be performed using predetermined grid coordinates of the contrasting edges. Insufficient visible light for clear contrasting image of pupil with frame camera 2330 is processed to provide an infrared filtered detection of eye for a clear contrasting image to determine pupil size 2340 of one embodiment.

Figure 24:
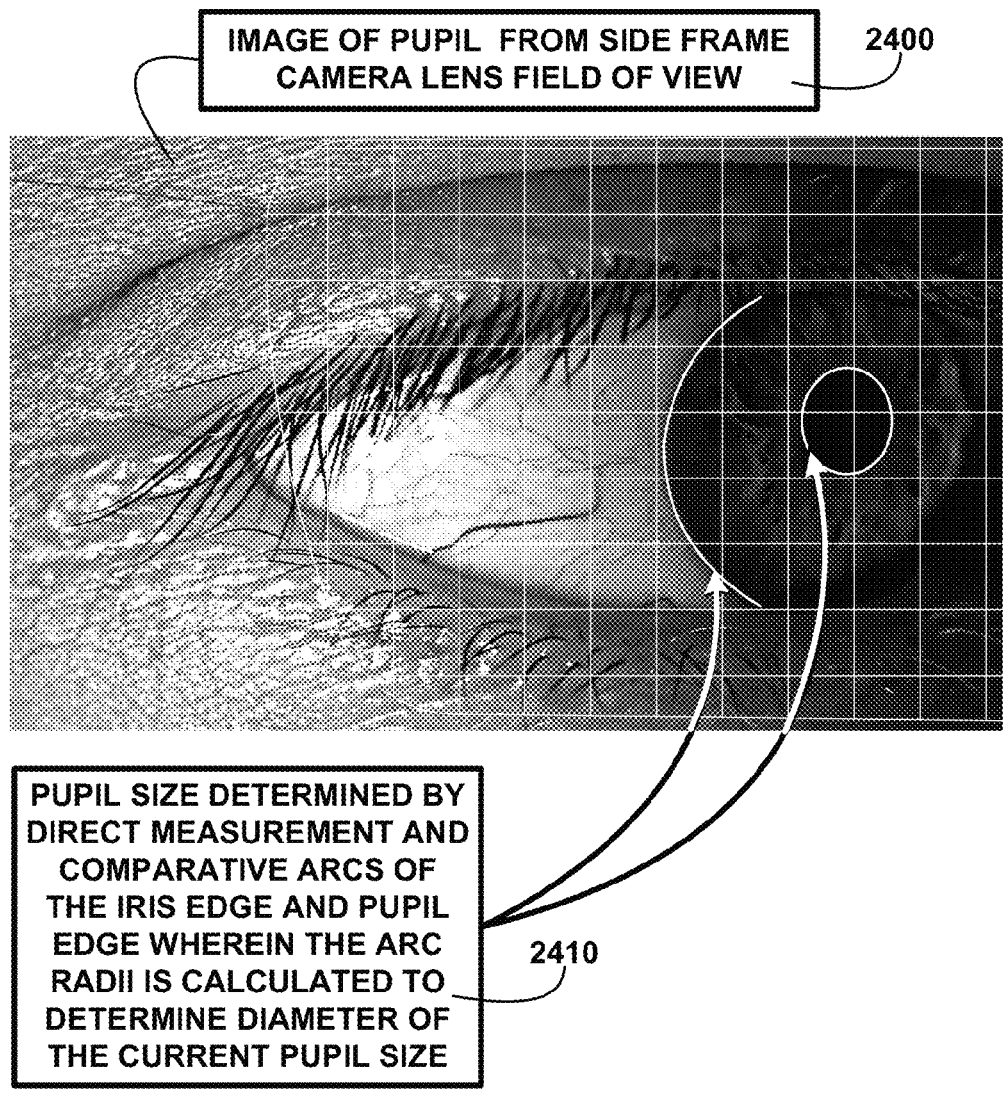
FIG. 24 shows for illustrative purposes only an example of pupil size arc measurements of one embodiment.

Pupil Size Arc Measurements:

FIG. 24 shows for illustrative purposes only an example of pupil size arc measurements of one embodiment. FIG. 24 shows an image of pupil from side frame camera lens field of view 2400 which does not give a full view of the pupil. The iris does not change, constrict or dilate on the outer perimeter. The constant iris perimeter arc shape can be used for each wearer's eyes to establish a benchmark for comparison to a fully dilated pupil arc and a fully constricted pupil arc. Comparing the current pupil arc can be compared to the iris arc. This comparison will improve a determination of the current pupil arc radius. Pupil size determined by direct measurement and comparative arcs of the iris edge and pupil edge wherein the arc radius is calculated to determine diameter of the current pupil size 2410 is shown to be accurate of one embodiment.

Figure 25:
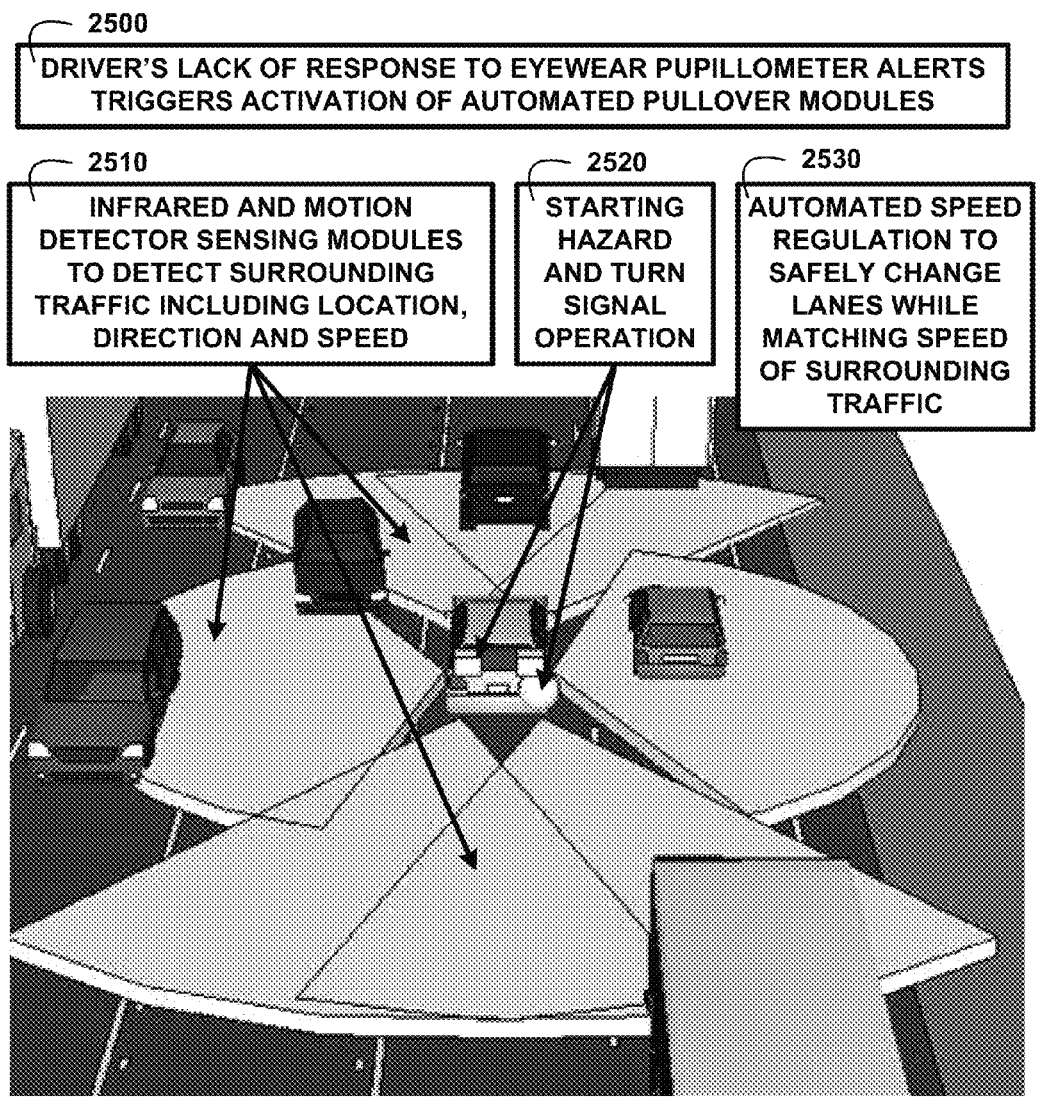
FIG. 25 shows for illustrative purposes only an example of automated pullover modules of one embodiment.

Automated Pullover Modules:

FIG. 25 shows for illustrative purposes only an example of automated pullover modules of one embodiment. FIG. 25 shows a driver's lack of response to eyewear pupilometer alerts, triggers activation of automated pullover modules 2500. Automated pullover modules use infrared and motion detector sensing modules to detect surrounding traffic including location, direction and speed 2510. An initial phase of operation is starting hazard and turn signal operation 2520. A concurrent operation is automated speed regulation to safely change lanes while matching speed of surrounding traffic 2530 of one embodiment.

Figure 26:
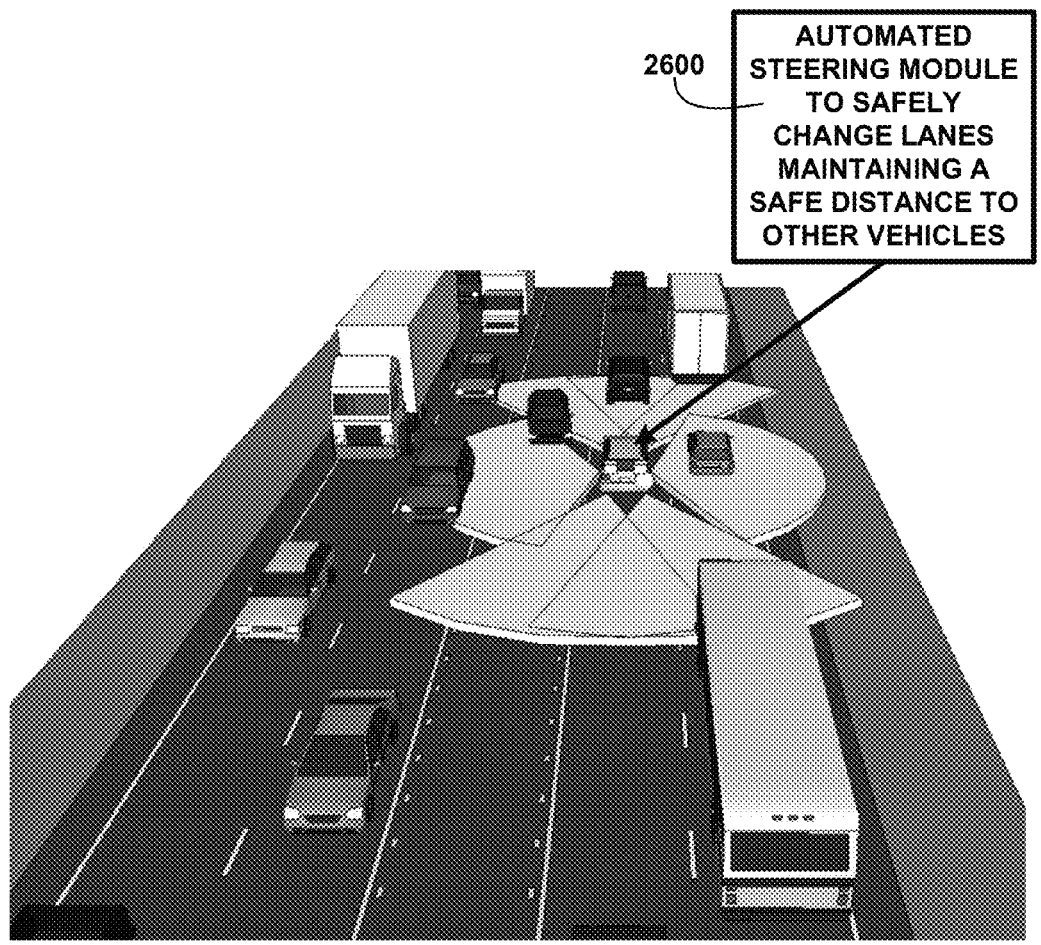
FIG. 26 shows for illustrative purposes only an example of automated steering module of one embodiment.

Automated Steering Module:

FIG. 26 shows for illustrative purposes only an example of automated steering module of one embodiment. FIG. 26 shows an automated steering module to safely change lanes maintaining a safe distance to other vehicles 2600 of one embodiment.

Figure 27:
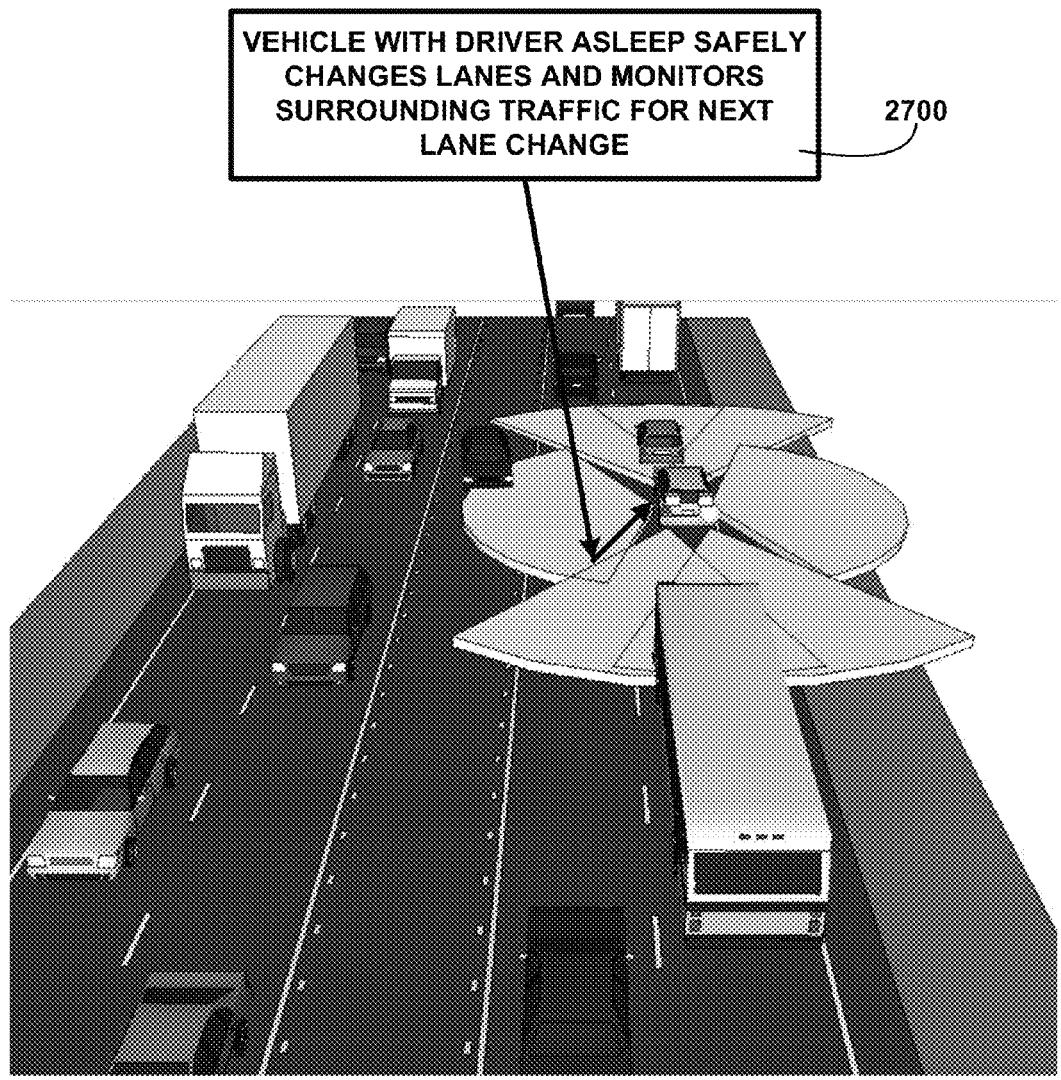
FIG. 27 shows for illustrative purposes only an example of monitoring surrounding traffic of one embodiment.

Monitoring Surrounding Traffic:

FIG. 27 shows for illustrative purposes only an example of monitoring surrounding traffic of one embodiment. FIG. 27 shows a vehicle with driver asleep safely changes lanes and monitors surrounding traffic for next lane change 2700 of one embodiment.

Figure 28:
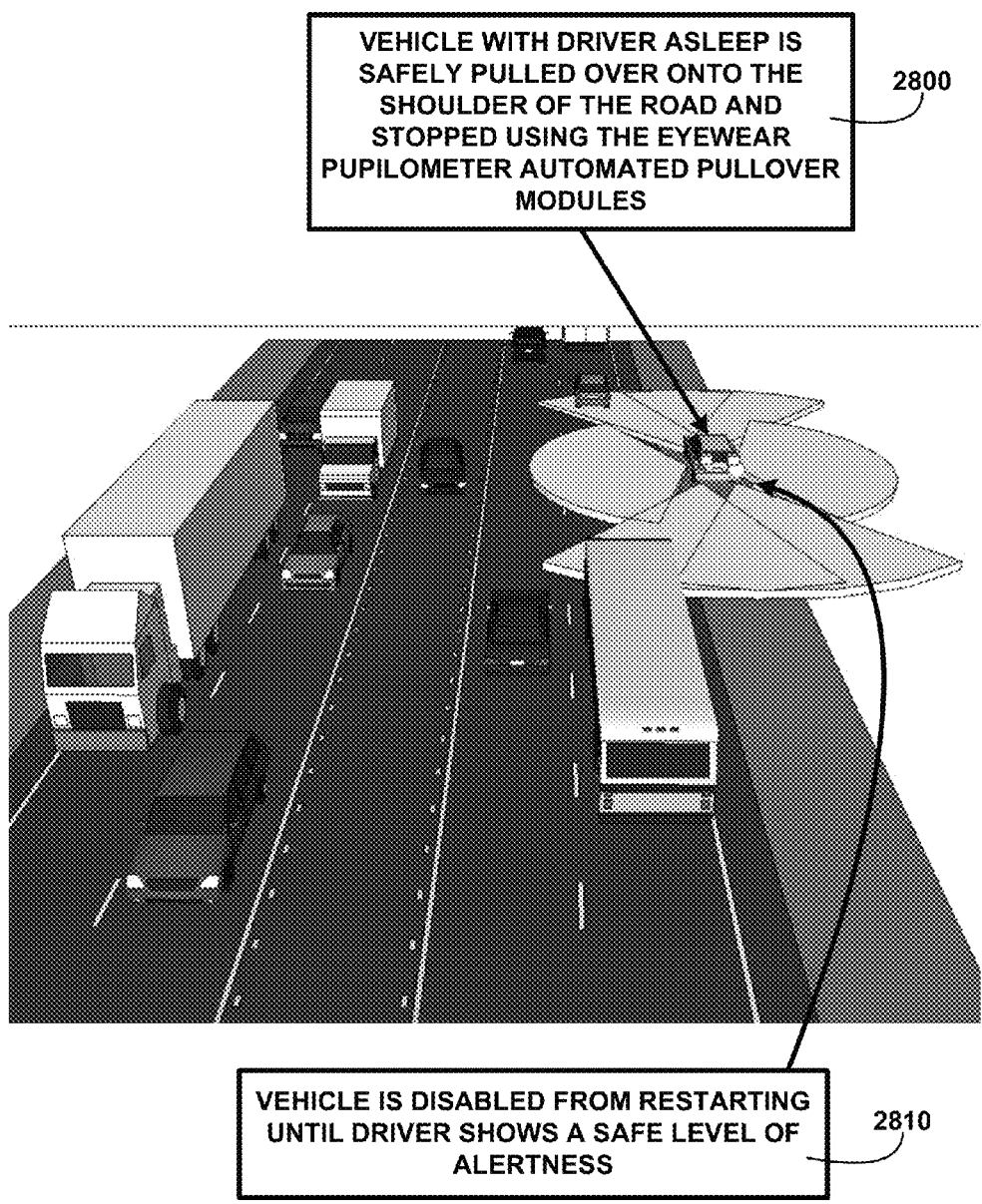
FIG. 28 shows for illustrative purposes only an example of disabling vehicle restart of one embodiment.

Disabling Vehicle Restart:

FIG. 28 shows for illustrative purposes only an example of disabling vehicle restart of one embodiment. FIG. 28 shows a vehicle with driver asleep is safely pulled over onto the shoulder of the road and stopped using the eyewear pupilometer automated pullover modules 2800. After stopping the vehicle is disabled from restarting until driver shows a safe level of alertness 2810 of one embodiment.

Figure 29:
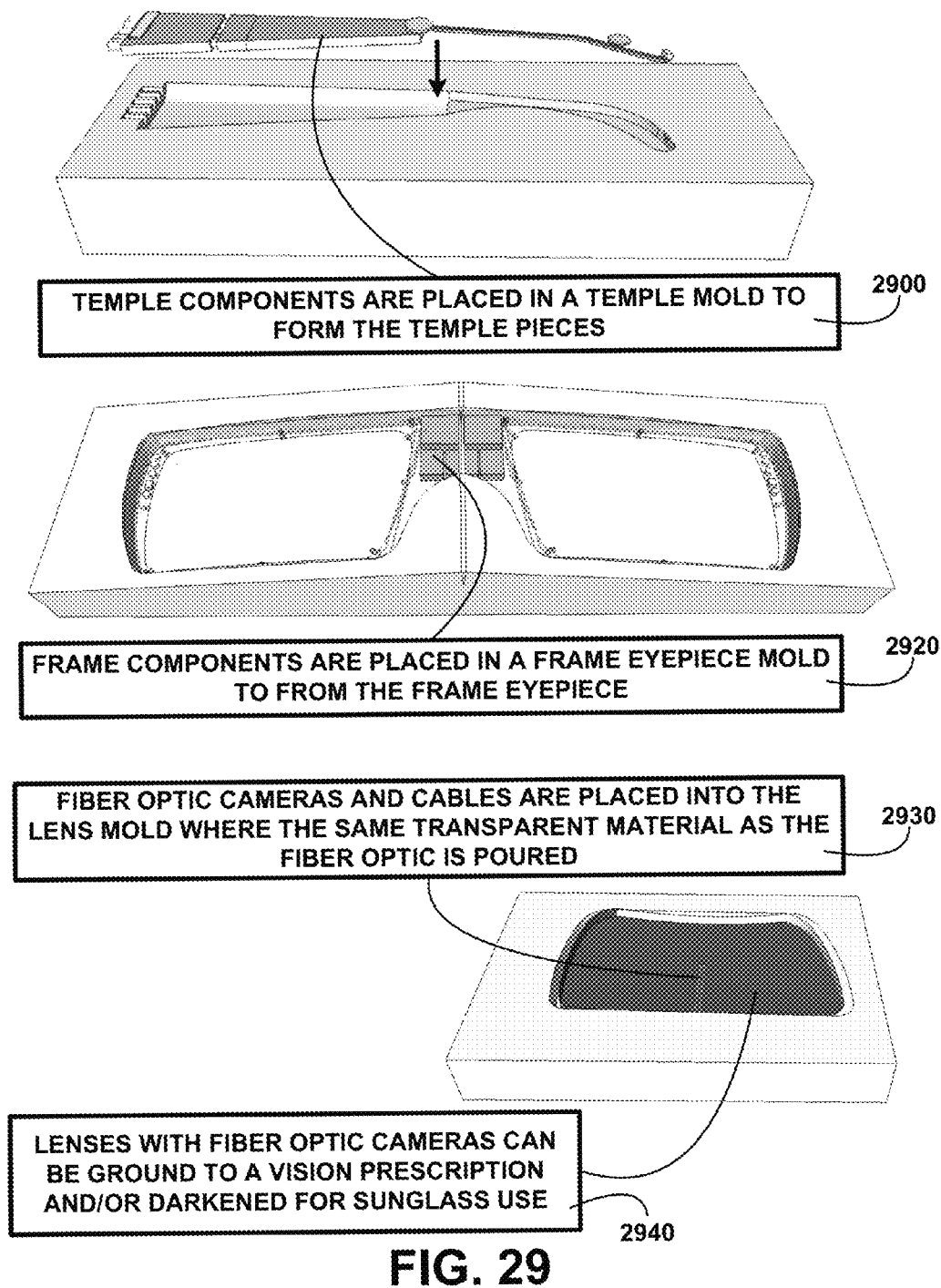
FIG. 29 shows for illustrative purposes only an example of eyewear pupilometer manufacturing of one embodiment.

Eyewear Pupilometer Manufacturing:

FIG. 29 shows for illustrative purposes only an example of eyewear pupilometer manufacturing of one embodiment. FIG. 29 shows temple components are placed in a temple mold to form the temple pieces 2900. Frame components are placed in a frame eyepiece mold to from the frame eyepiece 2920. Fiber optic cameras and cables are placed into the lens mold where a transparent lens material is poured 2930. Lenses with fiber optic cameras can be ground to a vision prescription and/or darkened for sunglass use 2940 of one embodiment.

Figure 30:
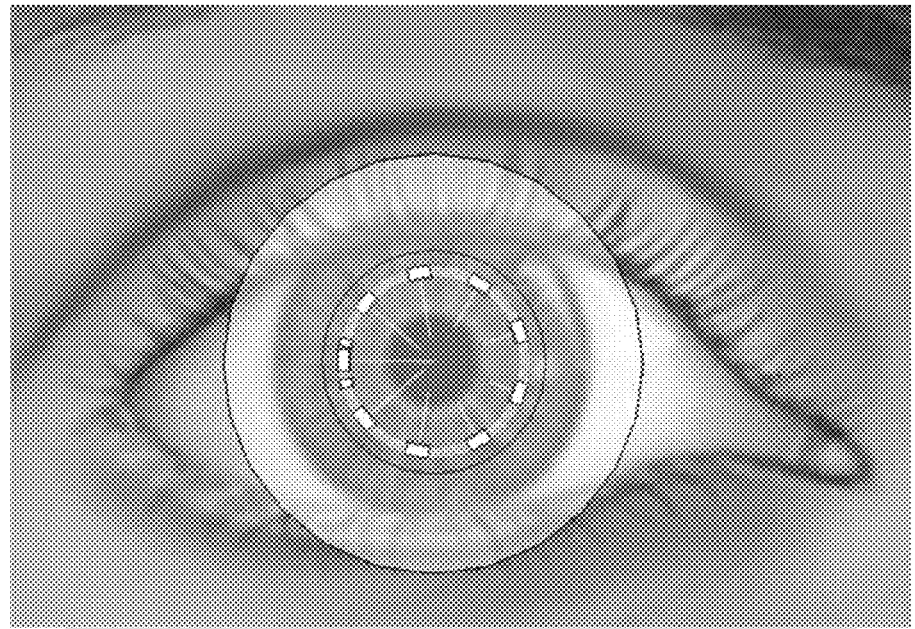
FIG. 30 shows for illustrative purposes only an example of eyewear pupilometer contact lenses worn on an eye of one embodiment.
Figure 30:
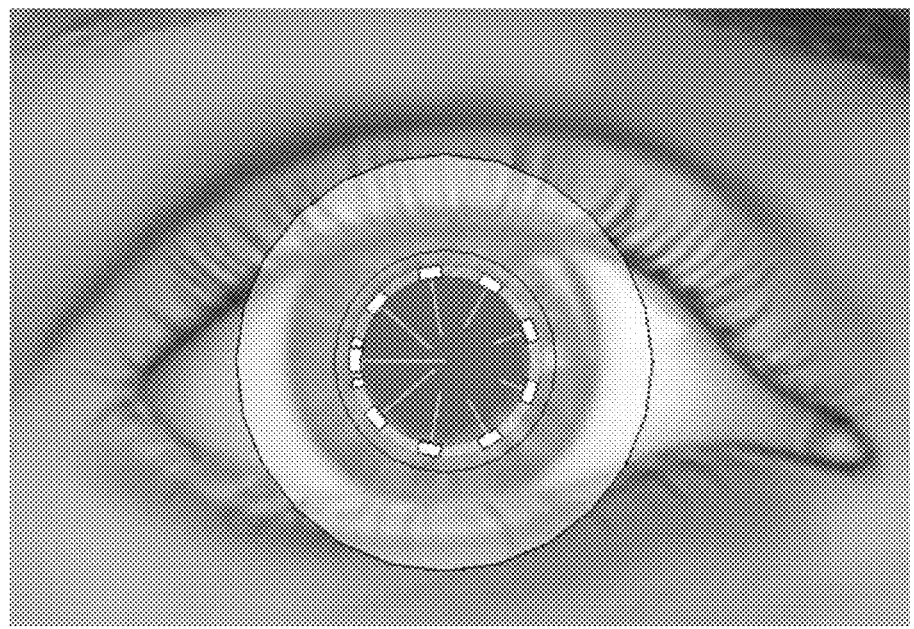

Eyewear Pupilometer Contact Lenses:

FIG. 30 shows for illustrative purposes only an example of eyewear pupilometer contact lenses worn on an eye of one embodiment. FIG. 30 shows an eyewear pupilometer contact lens shown on an eye with a constricted pupil 3000 and an eyewear pupilometer contact lens shown on an eye with a dilated pupil 3010. The fiber optic cameras are showing as white lines of varying lengths are shown in that manner to be visible in the illustration. The fiber optic cameras and contact lens materials are equally transparent. The central region of the contact lens is the corrective optics zone with a thickness that is determined by the type of contact lens design of one embodiment.

Conventional contact lenses include soft, hard, gas permeable (GP) and hybrid contact lens designs and materials. The average center thickness ranges from 0.08 to 0.18 millimeter (mm) or 80 to 180 micrometers (um) up to 800 um. A single-mode fiber has a core diameter of 8-10 um. Multi-mode fiber core diameters as small as 50 um of one embodiment.

Figure 31:
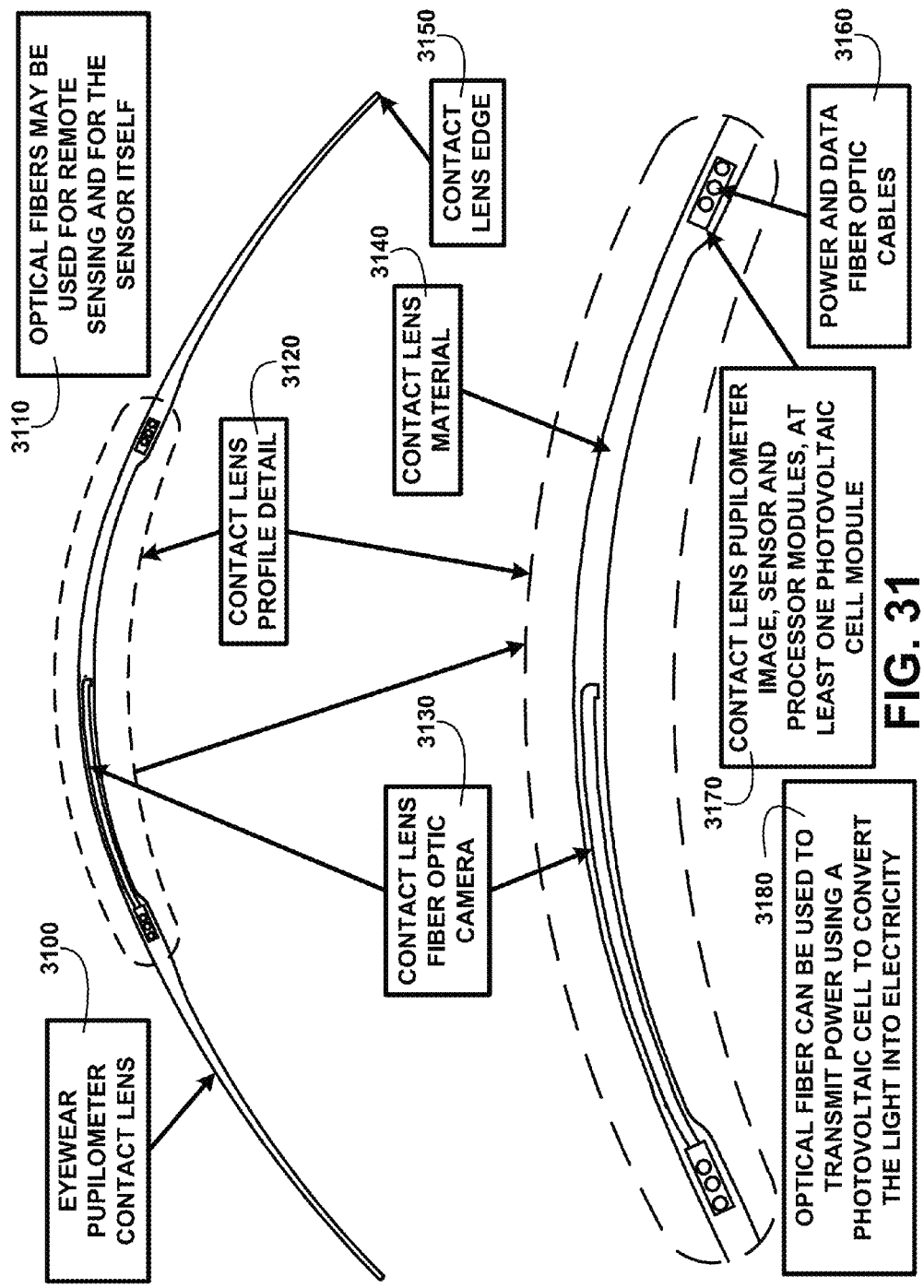
FIG. 31 shows for illustrative purposes only an example of an eyewear pupilometer contact lens cross section of one embodiment.

FIG. 31 shows for illustrative purposes only an example of an eyewear pupilometer contact lens cross section of one embodiment. FIG. 31 shows one embodiment of an eyewear pupilometer contact lens 3100. The eyewear pupilometer contact lens includes at least one contact lens fiber optic camera 3130. A contact lens edge 3150 is thinner than the central areas of the contact lens. FIG. 31 shows a contact lens profile detail 3120 that includes power and data fiber optic cables 3160 embedded into a contact lens material 3140. Also embedded into the contact lens material are other features of one embodiment that includes contact lens pupilometer image, sensor and processor modules, at least one photovoltaic cell module 3170. Optical fibers may be used for remote sensing and for the sensor itself 3110. Optical fiber can be used to transmit power using a photovoltaic cell to convert the light into electricity 3180 of one embodiment.

Figure 32:
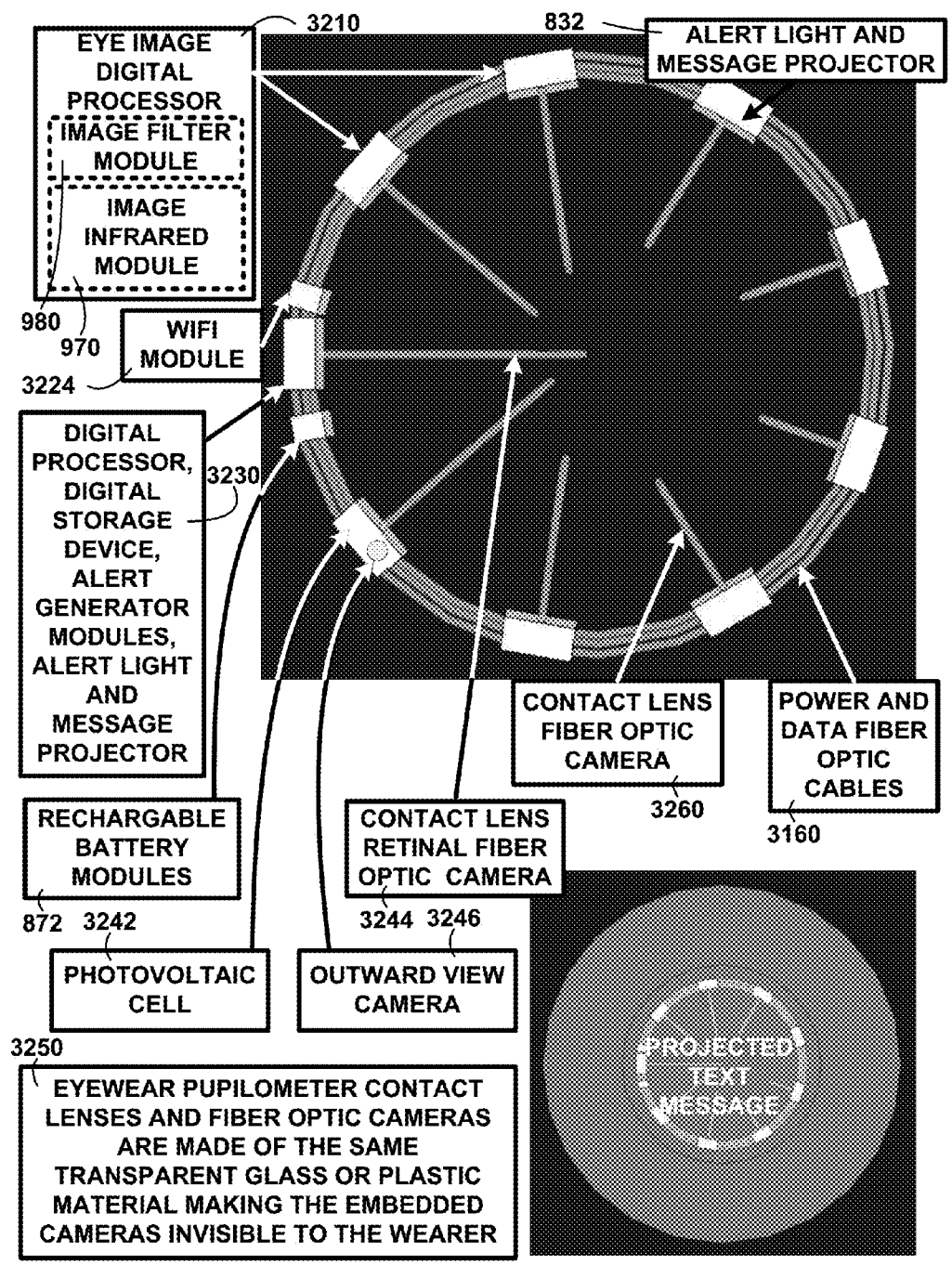
FIG. 32 shows for illustrative purposes only an example of eyewear pupilometer contact lens embedded structure of one embodiment.

Pupilometer Contact Lens:

FIG. 32 shows for illustrative purposes only an example of eyewear pupilometer contact lens embedded structure of one embodiment. FIG. 32 shows one embodiment of an eyewear pupilometer contact lens embedded structure including at least one eye image digital processor 3210, image filter module 980, image infrared module 970, alert light and message projector 832, contact lens fiber optic camera 3260, contact lens retinal fiber optic camera 3244, rechargeable battery modules 872, power and data fiber optic cables 3160, digital processor, digital storage device, alert generator modules, and WI-FI module. FIG. 32 shows at least one outward view camera 3246 and at least one photovoltaic cell 3242. The eyewear pupilometer contact lenses and fiber optic cameras may be made of transparent glass or plastic material making the embedded cameras nearly invisible to the wearer 3250 of one embodiment.

Figure 33:
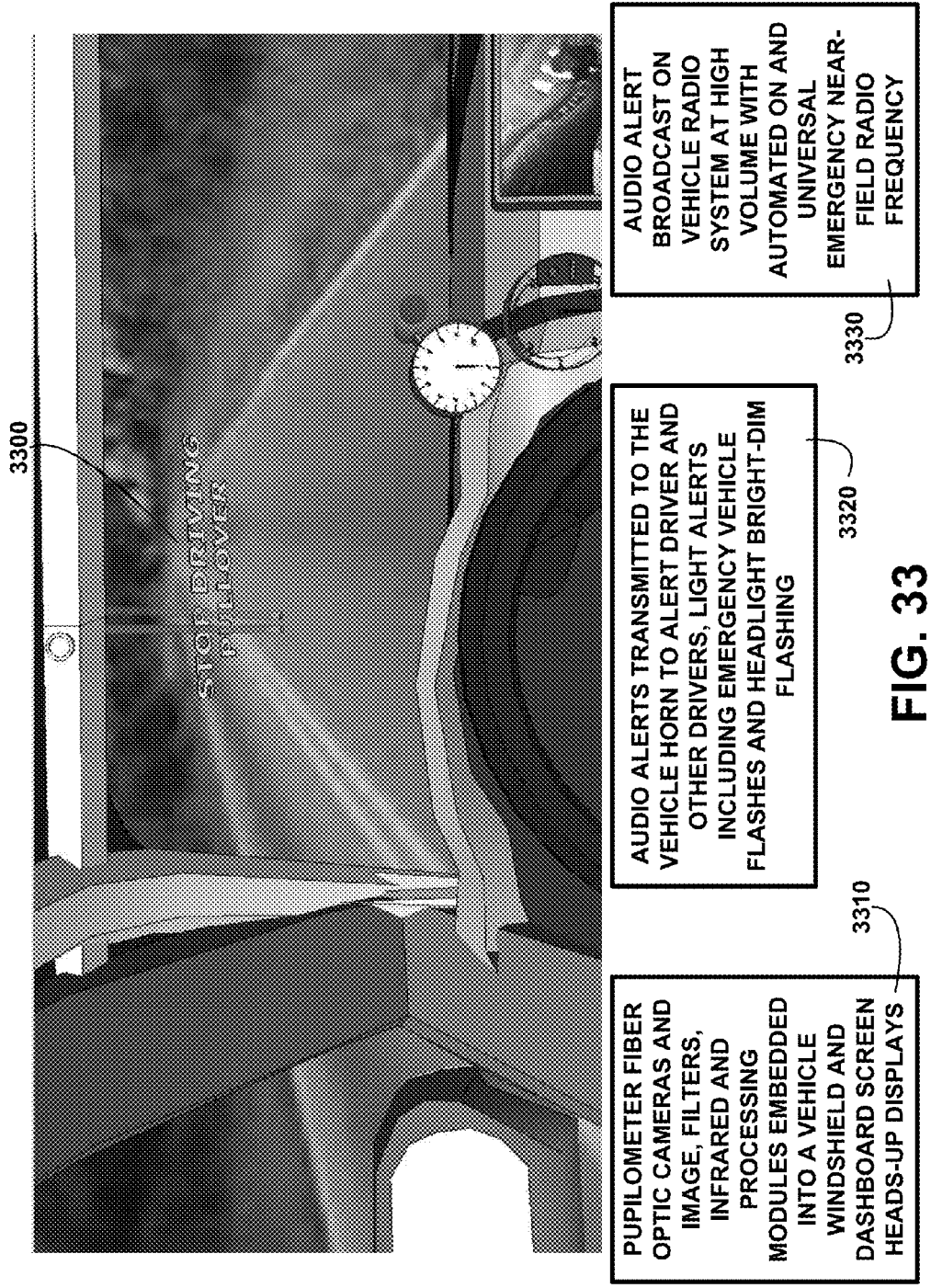
FIG. 33 shows for illustrative purposes only an example of eyewear pupilometer features embedded into a vehicle wind shield of one embodiment.

Eyewear Pupilometer Embedded into a Vehicle Windshield:

FIG. 33 shows for illustrative purposes only an example of eyewear pupilometer features embedded into a vehicle windshield of one embodiment. FIG. 33 shows pupilometer fiber optic cameras and image, filters, infrared and processing modules embedded into a vehicle windshield and dashboard screen heads-up displays 3310. The embedded windshield may be used for heads-up displays for example "STOP DRIVING PULLOVER" 3300. The pupilometer can broadcast audio alerts transmitted to the vehicle horn to alert the driver and other drivers, light alerts including emergency vehicle flashers and headlight bright-dim flashing 3320. Audio alert broadcast on vehicle radio system at high volume with automated on and universal emergency near-field radio frequency 3330 to awaken or cause the driver to become more aware of their drowsiness of one embodiment.

Figure 34:
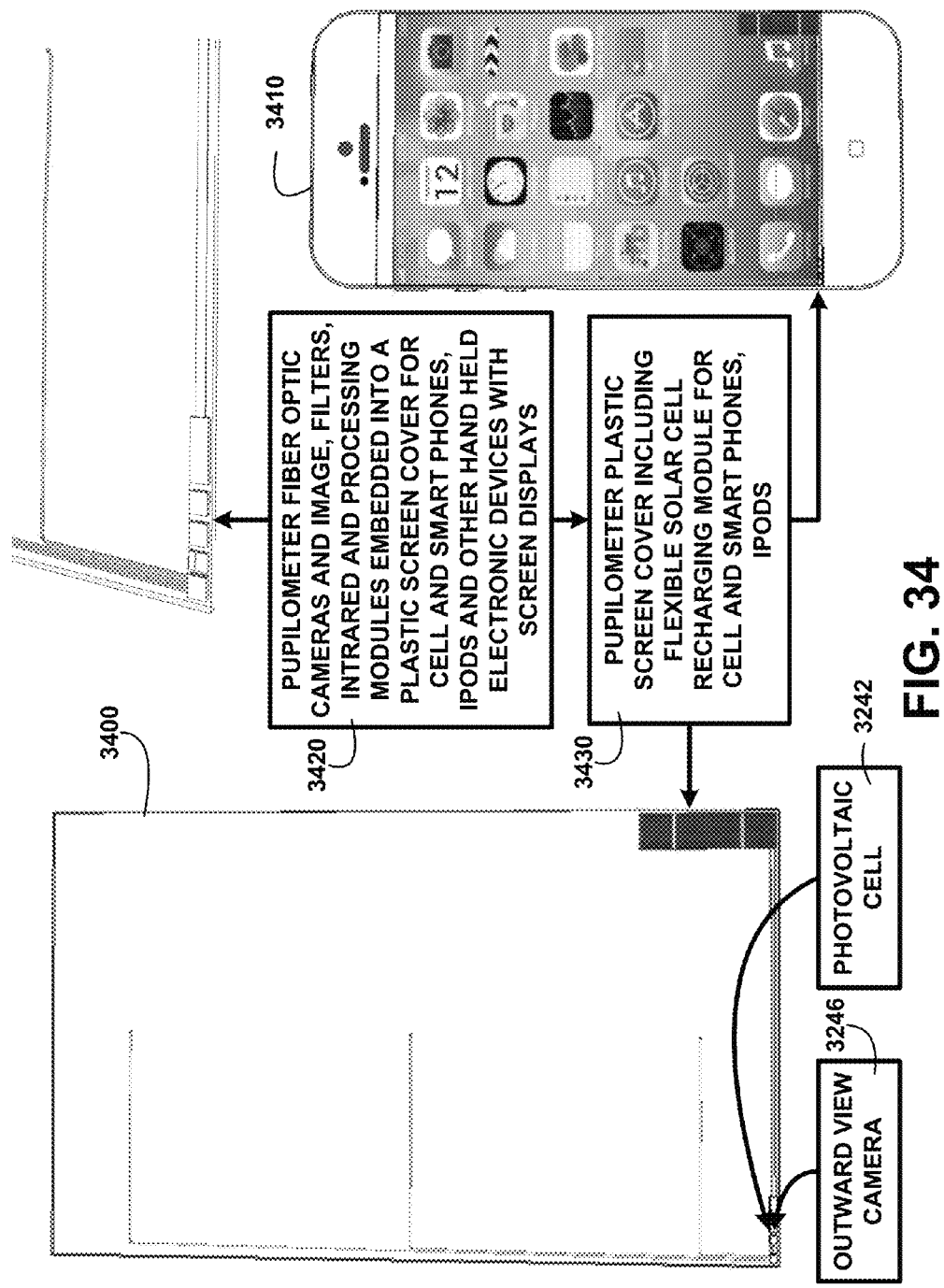
FIG. 34 shows for illustrative purposes only an example of an eyewear pupilometer hand held device protective cover of one embodiment.

Eyewear Pupilometer Smart Phone Protective Cover:

FIG. 34 shows for illustrative purposes only an example of an eyewear pupilometer hand held device protective cover of one embodiment. FIG. 34 shows pupilometer fiber optic cameras and image, filters, infrared and processing modules embedded into a plastic screen cover for cell and smart phones, iPods and other hand held electronic devices with screen displays 3420. The plastic cover 3400 includes at least one outward view camera 3246 and at least one photovoltaic cell 3242 fits over for example a smart phone 3410. The pupilometer plastic screen cover including flexible solar cell recharging module for cell and smart phones, iPods 3430 for powering the pupilometer plastic screen cover of one embodiment.

Figure 35:
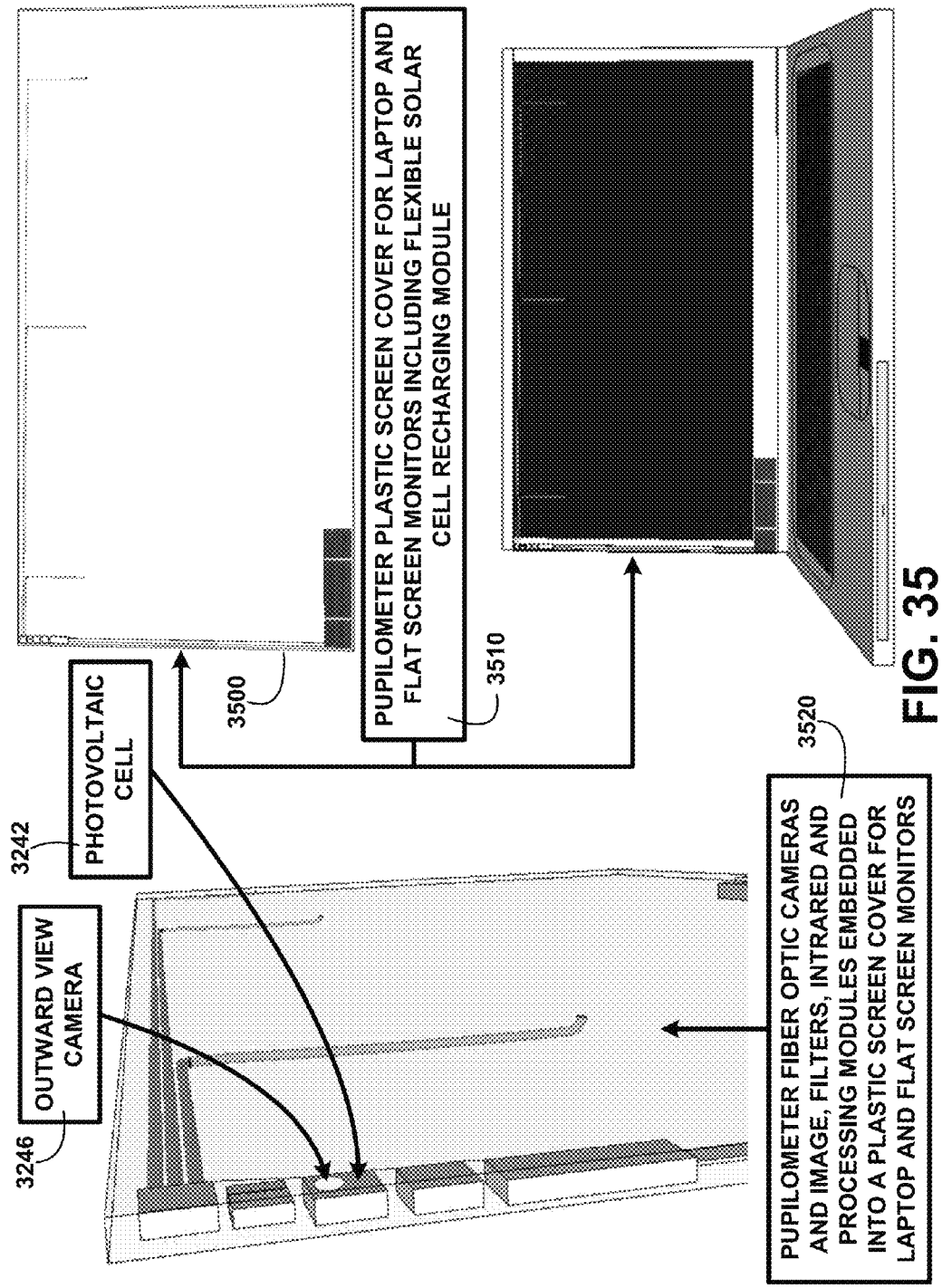
FIG. 35 shows for illustrative purposes only an example of an eyewear pupilometer display screen protective cover of one embodiment.

Eyewear Pupilometer Laptop Display Protective Cover:

FIG. 35 shows for illustrative purposes only an example of an eyewear pupilometer display screen protective cover of one embodiment. FIG. 35 shows pupilometer fiber optic cameras and image, filters, infrared and processing modules embedded into a plastic screen cover for laptop and flat screen monitors 3520. The pupilometer plastic cover for laptops 3500 includes at least one outward view camera 3246 and at least one photovoltaic cell 3242. Pupilometer plastic screen cover for laptop and flat screen monitors including flexible solar cell recharging module 3510 of one embodiment.

Figure 36:
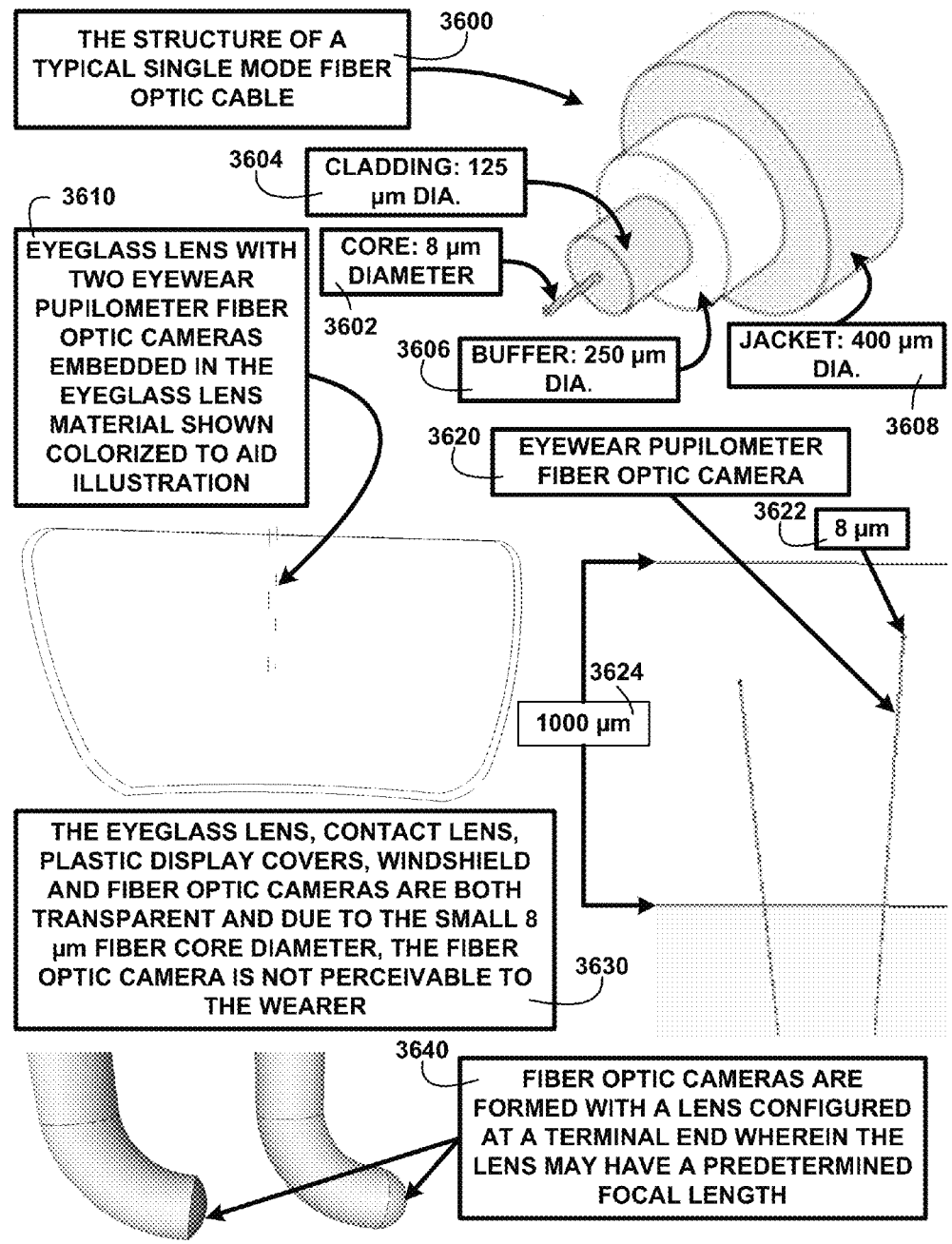
FIG. 36 shows for illustrative purposes only an example of an eyewear pupilometer fiber optic camera of one embodiment.

Eyewear Pupilometer Fiber Optic Camera:

FIG. 36 shows for illustrative purposes only an example of an eyewear pupilometer fiber optic camera of one embodiment. FIG. 36 shows a structure of a typical single-mode fiber optic cable 3600 includes a fiber core of an 8 μm diameter 3602, a transparent cladding material to keep light in the core with a 125 μm diameter 3604, a tough resin buffer layer that protects it from moisture and physical damage with a 250 μm diameter 3606, and a jacket layer to add strength with a 400 μm diameter 3608. The fiber core acts as a waveguide of one embodiment.

The eyewear pupilometer fiber optic camera 3620 and sensors modules in one embodiment include only the fiber core with no greater than an 8 μm diameter 3622. Where the fiber optic cameras are embedded in corrective eyeglass lenses the transparent eyeglass lens material provides the function of the cladding, eliminates the need for the buffer and jacket layers as the core is embedded in the eyeglass lens. The FDA maintains corrective eyeglass lens tests that require a minimum thickness that ranges for glass of 2.0 mm (2000 μm) to some newer materials down to 1.0 mm (1000 μm). FIG. 36 shows an example of an eyeglass lens with two eyewear pupilometer fiber optic cameras embedded in the eyeglass lens material shown colorized to aid illustration 3610. The eyeglass lens is shown with a thickness of 1000 μm 3624 and two eyewear pupilometer fiber optic cameras with a core diameter no greater than 8 μm embedded in the eyeglass lens material. The eyeglass lens, contact lens, plastic display covers, windshield and fiber optic cameras are both transparent and due to a fiber core diameter no greater than 8 μm, the fiber optic camera is not perceivable to the wearer 3630. Fiber optic cameras are formed with a lens configured at a terminus end wherein the lens may have a predetermined focal length 3640 of one embodiment.

Optical fiber may be used as sensors. Fibers have many uses in remote sensing. In some applications, the sensor is itself an optical fiber. In other cases, fiber is used to connect a non-fiber optic sensor to a measurement system. Depending on the application, fiber may be used because of its small size, or the fact that no electrical power is needed at the remote location, or because many sensors can be multiplexed along the length of a fiber by using different wavelengths of light for each sensor, or by sensing the time delay as light passes along the fiber through each sensor. Time delay can be determined using a device such as an optical time-domain reflectometer of one embodiment.

Optical fibers can be used as sensors to measure strain, temperature, pressure and other quantities by modifying a fiber so that the property to measure modulates the intensity, phase, polarization, wavelength, or transit time of light in the fiber. Sensors that vary the intensity of light are the simplest, since only a simple source and detector are required. A particularly useful feature of such fiber optic sensors is that they can, if required, provide distributed sensing over distances of up to one meter. Optical fiber can be used to transmit power using a photovoltaic cell to convert the light into electricity of one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the embodiments as defined by the following claims.

What is claimed is:

1. An apparatus, comprising:
   an eyewear pupilometer for detecting, measuring and processing a wearer's pupil movement and size, for detecting and processing retinal images, for detecting and processing a wearer's field of view, for broadcasting alerts, for pre-diagnostic screening, for overriding vehicle operation and for measuring, recording and transmitting circadian responses;
   at least one eyewear pupilometer module including a lens fiber optic camera module, an image processor module, a retinal image infrared detector module, an outward view camera module, an alert module, audio alert speaker module, an alert light and message projector, a WI-FI module, an automated pullover module, a vibration alert module, an automated steering module, an infrared and motion detector sensing modules, at least one vehicle windshield and dashboard screen heads-up display, fiber optic & data cables, a contact lens pupilometer image, sensor and processor module, a photovoltaic cell module;

wherein the outward view camera module may capture images in bright and darkened ambient light and the images captured may be processed in a face recognition processing module to aid the user in identifying someone whose name they forgot, or criminals that may accost the user and two outward view camera modules allow binocular views of objects and environmental features in the eyewear pupilometer user's field of vision for calculating triangulated distances and movements of outward viewed objects; and;

at least one eyewear pupilometer module coupled to and/or embedded into eyewear frame and lenses, contact lenses, a vehicle wind shield and a protective cover for a hand held device and/or a laptop computer.

2. The apparatus of claim 1, wherein the lens fiber optic camera module can be made of the same transparent glass or plastic material of an eyewear lenses making the embedded cameras invisible to the wearer.

3. The apparatus of claim 1, wherein the retinal image infrared detector module detects retinal images and processes sensor data using a lens infrared retinal fiber optic camera without the use of forced medication dilation of the pupils and without projecting potentially damaging light into the eye.

4. The apparatus of claim 1, wherein the alert light and message projector produces projected messages that are displayed onto the inside of the eyewear lenses including text messages that include "wake up", "pull over" and "stop driving", wherein the messages are varied in size, color and special effects including blinking, increasing light level or brightness, including bright flashes of light to arouse a driver wearing the eyewear pupilometer.

5. The apparatus of claim 1, further comprising overriding vehicle operation includes responding to alerts generated from calculated binocular view triangulated distances and movements that may be used in determining if the driver is swerving on the road to automatically activate the automated pullover module, automated steering module, infrared and motion detector sensing modules to safely slow, pull over and stop a vehicle being driven by a driver wearing the eyewear pupilometer.

6. The apparatus of claim 1, further comprising at least one eyewear pupilometer module embedded into a contact lens may include at least one eye image digital processor, image filter module, image infrared module, alert light and message projector, contact lens fiber optic camera, contact lens retinal fiber optic camera, rechargeable battery modules, power and data fiber optic cables, digital processor, digital storage device, alert generator modules, WI-FI module, at least one outward view camera and at least one photovoltaic cell.

7. The apparatus of claim 1, wherein at least one eyewear pupilometer module embedded into a contact lens is thinner than a contact lens central area and may be made of transparent glass or plastic material making the embedded module nearly invisible to the wearer.

8. The apparatus of claim 1, wherein the audio alert speaker module is used for producing non-regular audio sounds and verbal messages from a speaker integrated into an eyewear frame temples in proximity to each ear, wherein the sounds are varied in pitch and volume and frequency of broadcast to not form a harmonic rhythm or lulling sensation and is used for automatically alerting driver and authorities of the drowsy driver.

9. The apparatus of claim 1, wherein the vibration alert module is used for producing non-regular vibration alerts to a driver wearing an eyewear pupilometer to arouse the driver and wherein the non-regular vibration alerts are transmitted from eyewear frame temples in proximity to each ear boney areas, bridge of a nose through a frame nose piece, wherein a vibratory level, frequency and intensity are varied to not form a harmonic rhythm or lulling sensation.

10. An apparatus, comprising:

an eyewear pupilometer for detecting, measuring and processing a wearer's pupil movement and size, for detecting and processing retinal images, for detecting and processing a wearer's field of view, for broadcasting alerts, for pre-diagnostic screening, for overriding vehicle operation and for measuring, recording and transmitting circadian responses;

at least one eyewear pupilometer module including a lens fiber optic camera module, an image processor module, a retinal image infrared detector module, an outward view camera module, an alert module, audio alert speaker module, an alert light and message projector, a WI-FI module, an automated pullover module, a vibration alert module, an automated steering module, an infrared and motion detector sensing modules, at least one vehicle windshield and dashboard screen heads-up display, fiber optic & data cables, a contact lens pupilometer image, sensor and processor module, a photovoltaic cell module;

further comprising overriding vehicle operation includes responding to alerts generated from calculated binocular view triangulated distances and movements that may be used in determining if a driver wearing an eyewear pupilometer is swerving on a road to automatically activate the automated pullover module, automated steering module, infrared and motion detector sensing modules to safely slow, pull over and stop a vehicle being driven by a driver wearing the eyewear pupilometer and after stopping the vehicle it is disabled from restarting until driver shows a safe level of alertness; and;

at least one eyewear pupilometer module coupled to and/or embedded into eyewear frames and lenses, contact lenses, and vehicle wind shields.

11. The apparatus of claim 10, wherein two outward view camera modules allow binocular views of objects and environmental features in the eyewear pupilometer user's field of vision for calculating triangulated distances and movements of outward viewed objects.

12. The apparatus of claim 10, wherein the audio alert speaker module is used for producing non-regular audio sounds and verbal messages from a speaker integrated into an eyewear frame temples in proximity to each ear, wherein the sounds are varied in pitch and volume and frequency of broadcast to not form a harmonic rhythm or lulling sensation and is used for automatically alerting driver and authorities of the drowsy driver.

13. The apparatus of claim 10, wherein the vibration alert module is used for producing non-regular vibration alerts to a driver wearing an eyewear pupilometer to arouse the driver and wherein the non-regular vibration alerts are transmitted from eyewear frame temples in proximity to each ear boney areas, bridge of a nose through a frame nose piece, wherein a vibratory level, frequency and intensity are varied to not form a harmonic rhythm or lulling sensation.

14. An apparatus, comprising:
an eyewear pupilometer for detecting, measuring and processing a wearer's pupil movement and size, for detecting and processing retinal images, for detecting and processing a wearer's field of view, for broadcasting alerts, for pre-diagnostic screening, for overriding vehicle operation and for measuring, recording and transmitting circadian responses;
at least one eyewear pupilometer module including a lens fiber optic camera module, an image processor module, a retinal image infrared detector module, an outward view camera module, an alert module, audio alert speaker module, an alert light and message projector, a WI-FI module, an automated pullover module, a vibration alert module, an automated steering module, an infrared and motion detector sensing modules, at least one vehicle windshield and dashboard screen heads-up display, fiber optic & data cables, a contact lens pupilometer image, sensor and processor module, a photovoltaic cell module;
further comprising at least one eyewear pupilometer module embedded into a contact lens including at least one alert module for overriding vehicle operation to automatically activate the automated pullover module, automated steering module, infrared and motion detector sensing modules to safely slow, pull over and stop a vehicle being driven by a driver wearing the eyewear pupilometer and after stopping the vehicle it is disabled from restarting until driver shows a safe level of alertness; and:
at least one eyewear pupilometer module embedded into contact lenses.

15. The apparatus of claim 14, wherein at least one eyewear pupilometer module embedded into a contact lens is thinner than a contact lens central area and may include a fiber core diameter no greater than 8 μm and may be made of transparent glass or plastic material making the embedded module nearly invisible to the wearer.

16. The apparatus of claim 14, wherein the at least one eyewear pupilometer module embedded into a contact lens includes at least one photovoltaic cell to convert the light into electricity and at least one rechargeable battery module to store electricity for use in at least one eyewear pupilometer module coupled with at least one fiber optic cable to transmit power.

17. The apparatus of claim 14, further comprising at least one eyewear pupilometer module embedded into a contact lens including at least one pupilometer image, sensor and processor module.

* * * * *